US011980468B2

(12) United States Patent
Mendenhall et al.

(10) Patent No.: US 11,980,468 B2
(45) Date of Patent: *May 14, 2024

(54) WEARABLE CARDIAC ELECTROPHYSIOLOGY MEASUREMENT DEVICES, SOFTWARE, SYSTEMS AND METHODS

(71) Applicants: University of Pittsburgh—Of the Commonwealth System of Higher Education, Pittsburgh, PA (US); UPMC, Pittsburgh, PA (US)

(72) Inventors: George Stuart Mendenhall, Pittsburgh, PA (US); Matthew Jones, Pittsburgh, PA (US)

(73) Assignees: University of Pittsburgh—Of the Commonwealth System of Higher Education, Pittsburgh, PA (US); UPMC, Pittsburgh, PA (US)

( * ) Notice: Subject to any disclaimer, the term of this patent is extended or adjusted under 35 U.S.C. 154(b) by 407 days.

This patent is subject to a terminal disclaimer.

(21) Appl. No.: 17/078,527

(22) Filed: Oct. 23, 2020

(65) Prior Publication Data
US 2021/0052177 A1 Feb. 25, 2021

Related U.S. Application Data

(63) Continuation of application No. 15/560,297, filed as application No. PCT/US2016/025333 on Mar. 31, 2016, now Pat. No. 10,849,519.
(Continued)

(51) Int. Cl.
*A61B 5/25* (2021.01)
*A61B 5/00* (2006.01)
(Continued)

(52) U.S. Cl.
CPC .............. *A61B 5/25* (2021.01); *A61B 5/0006* (2013.01); *A61B 5/0022* (2013.01);
(Continued)

(58) Field of Classification Search
CPC ........ G16H 40/67; A61B 5/0408; A61B 5/25; A61B 5/0006; A61B 5/0022;
(Continued)

(56) References Cited

U.S. PATENT DOCUMENTS 4,230,127 A 10/1980 Larson
4,608,987 A 9/1986 Mills
(Continued)

FOREIGN PATENT DOCUMENTS

DE 19707681 C1 5/1998
DE 10048746 A1 4/2002
(Continued)

OTHER PUBLICATIONS

"ETMResource.com, 12-Lead ECG Placement, 2014, ETMResource. com, http://www.emtresource.com/resources/ecg/12-lead-ecg-placement/" (Year: 2014).*
(Continued)

*Primary Examiner* — Joseph M Dietrich
*Assistant Examiner* — Michael T. Holtzclaw
(74) *Attorney, Agent, or Firm* — Klarquist Sparkman, LLP

(57) ABSTRACT

Disclosed are wearable devices, such as rings and bracelets, for monitoring and diagnosing cardiovascular conditions of a wearer, along with related systems, algorithms and methods. The disclosed wearable devices can continuously monitor the wearer's cardiovascular status by measuring heart rate, motion, blood oxygenation, and/or other properties of the wearer. Disclosed wearable devices can further comprise three EKG electrodes, including a first electrode on the inner
(Continued)

surface adapted to detect a signal from the finger/wrist, a second electrode on the outer surface adapted to detect a cardiovascular signal from a finger of the opposing hand, and a third electrode on the outer surface of the frame adapted to detect a cardiovascular signal from a EKG lead location on the wearer's chest or leg. The wearable devices can be linked wirelessly to a mobile device that the person can interact with, and can further be linked to other distributed system components and healthcare providers.

24 Claims, 23 Drawing Sheets

Related U.S. Application Data

(60) Provisional application No. 62/140,671, filed on Mar. 31, 2015.

(51) Int. Cl.
| | |
|---|---|
| A61B 5/0205 | (2006.01) |
| A61B 5/024 | (2006.01) |
| A61B 5/11 | (2006.01) |
| G16H 40/67 | (2018.01) |
| G16Z 99/00 | (2019.01) |
| A61B 5/1455 | (2006.01) |
| A61B 5/349 | (2021.01) |
| A61B 5/389 | (2021.01) |
| A61N 1/04 | (2006.01) |

(52) U.S. Cl.
CPC ........ *A61B 5/0205* (2013.01); *A61B 5/02438* (2013.01); *G16H 40/67* (2018.01); *G16Z 99/00* (2019.02); *A61B 5/11* (2013.01); *A61B 5/14552* (2013.01); *A61B 5/349* (2021.01); *A61B 5/389* (2021.01); *A61B 5/6826* (2013.01); *A61B 5/683* (2013.01); *A61B 5/7275* (2013.01); *A61N 1/048* (2013.01)

(58) Field of Classification Search
CPC ..... A61B 5/0205; A61B 5/02438; A61B 5/11; A61B 5/14552; A61B 5/349; A61B 5/389; A61B 5/6826; A61B 5/683; A61B 5/7275; G16Z 99/00; A61N 1/048
USPC .......................................................... 600/509
See application file for complete search history.

(56) References Cited

U.S. PATENT DOCUMENTS

| | | | |
|---|---|---|---|
| 5,289,824 A | | 3/1994 | Mills et al. |
| 5,339,823 A | | 8/1994 | Reinhold, Jr. |
| 5,465,727 A | | 11/1995 | Reinhold, Jr. |
| 7,266,405 B1 | | 9/2007 | Alroy et al. |
| 8,460,189 B2 | * | 6/2013 | Libbus .................. A61B 5/327 |
| | | | 600/386 |
| 2002/0045836 A1 | | 4/2002 | Aklawwas |
| 2002/0111777 A1 | | 8/2002 | David |
| 2003/0187363 A1 | | 10/2003 | Alroy |
| 2005/0165319 A1 | | 7/2005 | Brodnick et al. |
| 2006/0025695 A1 | | 2/2006 | Wei |
| 2006/0047212 A1 | * | 3/2006 | Wei ....................... A61B 5/327 |
| | | | 600/509 |
| 2006/0111640 A1 | | 5/2006 | Shen et al. |
| 2006/0224071 A1 | | 10/2006 | Stewart |
| 2008/0234592 A1 | | 9/2008 | Lim et al. |
| 2009/0264782 A1 | | 10/2009 | Pearlman |
| 2010/0069735 A1 | | 3/2010 | Berkner |
| 2010/0076331 A1 | | 3/2010 | Chan et al. |
| 2010/0124920 A1 | | 5/2010 | Feher |
| 2010/0286532 A1 | | 11/2010 | Farringdon et al. |
| 2011/0105928 A1 | | 5/2011 | Bojovic et al. |
| 2012/0029318 A1 | * | 2/2012 | Kuo ....................... A61B 5/318 |
| | | | 600/301 |
| 2012/0316420 A1 | * | 12/2012 | Ordonez-Smith ..... A61B 5/318 |
| | | | 600/523 |
| 2014/0081118 A1 | * | 3/2014 | Reinhold, Jr. ......... A61B 5/332 |
| | | | 600/384 |
| 2014/0275850 A1 | * | 9/2014 | Venkatraman ..... A61B 5/02427 |
| | | | 600/595 |
| 2014/0275919 A1 | * | 9/2014 | Katra ................... A61B 5/0031 |
| | | | 600/374 |
| 2015/0087933 A1 | * | 3/2015 | Gibson .................. A61B 5/002 |
| | | | 600/301 |
| 2015/0117161 A1 | * | 4/2015 | Nichol ................. G04B 47/063 |
| | | | 368/10 |
| 2016/0066805 A1 | * | 3/2016 | Scherf .................. A61B 5/0024 |
| | | | 600/523 |
| 2016/0228025 A1 | | 8/2016 | Dusan |
| 2016/0270668 A1 | * | 9/2016 | Gil ...................... A61B 5/02416 |
| 2016/0331273 A1 | * | 11/2016 | Armoundas ........... A61B 5/282 |
| 2016/0349803 A1 | | 12/2016 | Dusan |
| 2018/0064356 A1 | | 3/2018 | Mendenhall et al. |

FOREIGN PATENT DOCUMENTS

| | | |
|---|---|---|
| EP | 1188412 A2 | 4/2007 |
| JP | 2007-195693 | 8/2007 |
| KR | 10-2011-0012784 | 2/2011 |
| WO | WO2004/038942 A1 | 5/2004 |
| WO | WO 2015/030712 | 3/2015 |
| WO | WO 2016/161152 | 10/2016 |

OTHER PUBLICATIONS

International Search Report and Written Opinion for related International Application No. PCT/US2016/025333, dated Jun. 27, 2016, 15 pages.

* cited by examiner

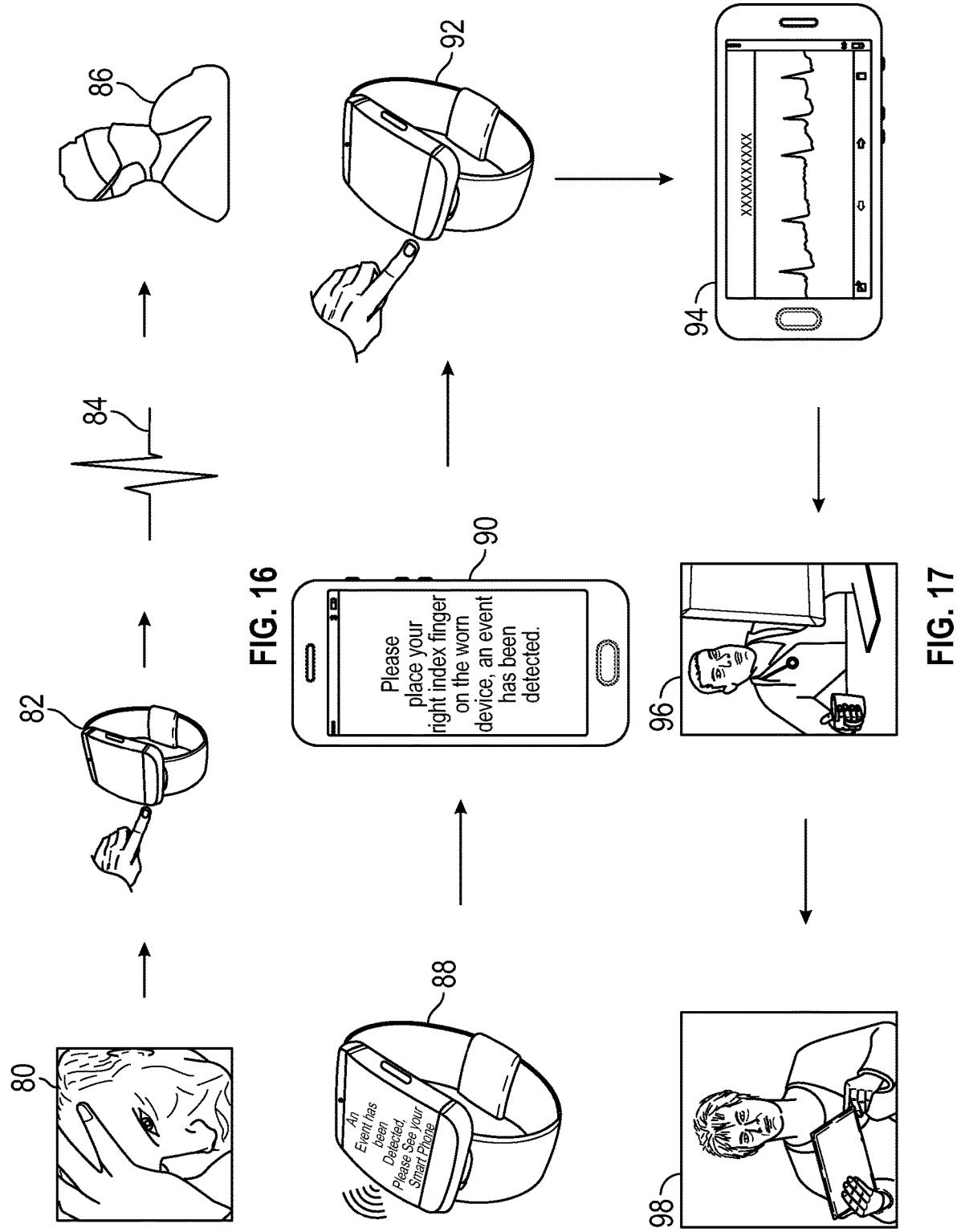

WEARABLE CARDIAC ELECTROPHYSIOLOGY MEASUREMENT DEVICES, SOFTWARE, SYSTEMS AND METHODS

CROSS-REFERENCE TO RELATED APPLICATIONS

This application is a continuation of U.S. patent application Ser. No. 15/560,297, filed Sep. 21, 2017, which is the U.S. National Stage of International Application No. PCT/US2016/025333, filed Mar. 31, 2016, which claims the benefit of U.S. Provisional Patent Application No. 62/140,671, filed Mar. 31, 2015, all of which are incorporated by reference herein in their entirety.

ACKNOWLEDGMENT OF GOVERNMENT SUPPORT

This invention was made with government support under (IIP-1449702) awarded by the (National Science Foundation) and with government support under (TR000005) awarded by the National Institutes of Health. The government has certain rights in the invention.

FIELD OF THE DISCLOSURE

This application relates to wearable electronic measurement and computing devices, and related systems, for use in cardiovascular healthcare.

BACKGROUND

Heart disease, stroke and other cardiovascular diseases are leading global causes of death. However, many cardiovascular diseases are preventable through early detection and treatment (e.g., of arrhythmia or atrial fibrillation), attention to genetic predisposition, nutrition, and activities of daily living. Multiple forces worsen the current situation, including the aging population, finite capacity to deliver care to at risk populations, the tendency to provide care in an episodic clinical environment as opposed to real-time continuous care delivery, and the pressure to reduce the cost of healthcare. The ratio of those needing care to those capable of providing care continues to rise resulting in a growing need for systems and tools capable of remote monitoring and care delivery to high risk populations.

Current wearable devices do not have the ability to reconstruct leads from a traditional 12 lead EKG. In addition, they lack the capacity to continuously monitor and evaluate events reflective of arrhythmias and other cardiovascular conditions. FDA cleared, non-invasive, ambulatory devices lack the ability for long term patient monitoring, potentially missing clinically relevant events.

SUMMARY

The disclosed technology provides wearable devices and related systems and methods for monitoring and determining cardiovascular conditions of a wearer.

Disclosed wearable devices can comprise a wearable band (e.g., a ring or bracelet) comprising an annular or partially annular frame configured to be worn around a first body part of a person (e.g., a finger or wrist or arm), the frame having an inner surface that faces the first body part and an outer surface that faces away from the first body part. The band can further comprise a first electrode on the inner surface of the frame adapted to detect a cardiovascular signal from the first body part, a second electrode on the outer surface of the frame adapted to detect a cardiovascular signal from a second body part of the wearer (e.g., a finger of the opposing hand) when the second body part is touched against the second sensor, and a third electrode on the outer surface of the frame, generally opposite from the second electrode, adapted to detect a cardiovascular signal from a EKG lead location on the wearer's body (e.g., the chest or leg) when the third electrode is touched against the EKG lead location while being worn on the first body part.

Some disclosed wearable devices can further comprise a sensor on the inner surface of the frame for measuring blood oxygen saturation of the wearer, a sensor on the inner surface of the frame for measuring bioimpedence of the skin of the first body part or dry skin potential between two separated points on the skin of the first body part, and/or other sensors on the inner surface of the device. Such sensors can be adapted to continuously monitor the wearer's cardiovascular status while the wearer is wearing the device to detect or predict cardiac arrhythmia or other cardiac abnormalities in the wearer.

Some disclosed wearable devices can simulate a 12-lead EKG by touching the third sensor to a plurality of EKG lead locations on the wearer's body while simultaneously touching the second body part to the second electrode. At each EKG location, the on-off status and polarity of each of the three electrodes can be configured to simulate one or more different traces of a conventional 12-lead EKG.

Also described herein are cardiac monitoring systems that can comprise any of the disclosed wearable device and a mobile computing device paired with the wearable device via wireless communication. The system can also include distributed elements, such as cloud servers, medical records databases, and computing devices associated with healthcare personnel associated with the person.

Some disclosed methods comprise: continuously monitoring a person's heart rate, motion, and/or blood oxygen levels using a device worn by the person; and based on the monitoring, determining potential arrhythmia in the person. The methods can further comprise determining that the person's heart rate is outside of a predetermined threshold range; assessing the level of the person's motion; determining whether purposeful motion is occurring, and/or determining whether blood oxygen levels are above or below a threshold value. Based on the assessments and determinations, the method can include prompting the person to input information regarding their symptoms. The methods can further comprise recommending treatment actions, such as vagal maneuvers, contacting related people with warning, sending alerts to the person, and/or notifying emergency services.

Some disclosed methods comprise: inducing a person to place a device worn by the person on a first body part against a first EKG lead location (e.g., chest or leg) on the person's body, such that a first electrode of the device contacts the first body part on which the device is worn and such that a second electrode of the device contacts the first EKG lead location, wherein the first body part is part of a first limb of the person (e.g., a finger or wrist or arm); inducing the person to place a second body part against a third electrode of the device while the second electrode is in contact with first EKG lead location and the first electrode is in contact with the first body part, wherein the second body part is part of a second limb of the person (e.g., finger on opposite hand); and obtaining EKG signals from the person using the first, second, and third electrodes of the device. EKG signals obtained using such methods can simulate EKG signals obtained using conventional 12-lead EKG devices.

The foregoing and other features and advantages of the disclosed technology will become more apparent from the following detailed description, which proceeds with reference to the accompanying figures.

BRIEF DESCRIPTION OF THE DRAWINGS

FIG. 16 is a flow chart illustrating an exemplary method wherein a person experiences symptoms, initiates cardiovascular measurement using the worn bracelet, and the data is transmitted to a health care provider for interpretation.

FIG. 17 is a flow chart illustrating an exemplary method wherein the worn bracelet determines that a cardiovascular event may have occurred and prompts the wearer to initiate cardiovascular measurement using the worn bracelet, and the data is transmitted via a linked mobile computing device to health care providers for interpretation and follow-up health care.

DETAILED DESCRIPTION

Figure 1:
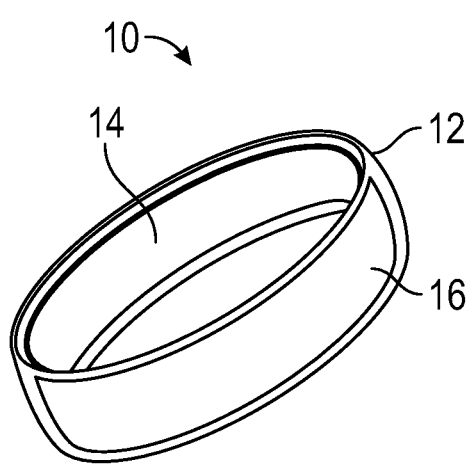
FIGS. 1 and 2 show an exemplary wearable ring that includes sensors and other technology for measuring physiological properties of the wearer to monitor and/or diagnose cardiovascular health conditions.

Disclosed herein are wearable devices, related systems, and methods for monitoring, measuring, diagnosing, analyzing, storing and/or communicating cardiovascular health conditions, such as arrhythmia, coronary blockage, infarction, ischemia, bradycardia, tachycardia, stroke, etc., and related data for the person wearing the device. The wearable devices can include bands or other devices worn on or around various body parts, such as a finger, wrist, arm, ankle, leg, abdomen, chest, neck, and/or any combination thereof. As used herein, the term "wrist" means any part of the arm from the hand to the elbow, including the narrow part of the forearm around the ulna and radius, and is not limited to just the wrist joint(s). The term "wrist" is meant to include any part of the arm where a bracelet or wrist band may be worn. Specific examples of wearable bands include rings, bracelets, watches, hand bands, arm bands, anklets, and leg bands. Related systems can include a mobile computing device operated by the wearer or another person associated with the wearer, such as smartphones, tablet computers, personal computers, etc. Related systems can further include distributed elements, such as cloud based servers, health records databases, emergency service providers, relatives or other contacts, and/or health care providers. The wearable device and/or other system components can include processors, memory, wired and wireless communication systems, power supplies and recharging means, user interface devices, and/or other components. Further, various software programs, algorithms, firm wear, computer readable media and storage devices, and/or other means for storing or accessing computer readable instructions for implementing disclosed algorithms and methods can be included in the disclosed technology.

The disclosed wearable device can include sensors and/or other technology configured to measure or determine various characteristics and signals associated with the physiological properties of the wearer and electrophysiological or electromyography functions of the human heart and cardiovascular system. Exemplary sensors can include sensors for measuring heart rate, oxygen saturation levels of blood, blood pressure, EKG signals, temperature, electrical transmissivity of the skin, physical multi-axis motion and acceleration of the wearer orientation of the wearer, location of the wearer, time, and/or other properties and activities of the wearer. For example, the device or system can calculate algorithmically blood pressure using methods correlating systolic blood pressure and applying techniques such as Pulse Transit Time (PTT) and Pulse Wave Velocity (PWV). Such information can be recorded, analyzed, stored, and/or communicated to other system components. The wearable devices sensors may comprise, for example, an infrared emitter-detector pair to measure blood oxygen saturation, PTT, and/or PWV, galvanic skin sensors, a silver nanowire to measure bioimpedence or dry skin potential between two separated points on the body, a multi-axis accelerometer, a magnetometer, a gyroscope, a heat flux sensor, GPS device, and/or various other sensors.

The cardiac electrophysiology measurement and condition management system, tools, devices, and methods disclosed herein can enable profiling, customization, and/or personalization of a window which defines, on an individual basis, an aberrant or life threatening event which could trigger an alert to 911, EMS or other caregiver. Measured and/or determined characteristics of the wearer can be compared to analogues to medical standards, such as sinus rhythm standards including the PR Interval, the PR Segment, the QRS Complex, the ST Segment and/or the QT Interval, to determine the existence of an aberrant or life threatening event or condition.

Disclosed devices can also include various user interface features, such as a display, hard and/or soft input panels, vibration or haptic notification devices, audio notification devices, lights or other visual notification devices, microphones or audio receivers, and wireless communication systems such as wifi, Bluetooth, Bluetooth Low Energy, near-field RF, cellular, etc. Disclosed devices and systems may also include voice activation and interaction capabilities utilizing voice recognition functionality, such as SIRI or Dragon Voice recognition software, which can be used for example to initiate an "I need help" sequence triggering an alert to 911, EMS or other caregiver action.

In some embodiments, feedback regarding aggregate clinical status is immediately relayed to the patient for change in medical therapy based on the cardiac rhythm observed from the device at the current time or via specified integrative criteria of past time. This may occur without use of any ancillary devices and communicated by the device itself via flashing indicator, color change, tactile alert, or other indicator.

Disclosed methods can include continuous monitoring and/or automated detection of aberrant or life threatening changes in heart rate, motions, oxygenations, and/or other characteristics, reflective of arrhythmic events, derived from combining and processing multiple inputs from the wearable devices. Some disclosed methods can include real time synthesis of any one, multiple selected, or all of the traces of a full 12 lead EKG set using signal-averaged techniques and algorithms by touching of the wearable device(s) to different parts of the body and incorporating any or all of the resident sensors. For example, in an exemplary method, upon sensing a potential arrhythmia, the wearer can generate a full 12-lead EKG using electrodes in the ring/bracelet and visual cues from a paired smart phone application, whereupon the smart phone application assesses the EKG data and/or transfers EKG data to a cloud based server for assessment. Abnormal EKG strips can then be delivered to pre-designated healthcare providers and/or emergency personnel. In addition, warning messages can be delivered to family members or other associates of the wearer.

Some methods can include aggregation and analysis of non-patient specific data sets to identify high risk individuals, inform population management methods, enhance the standard of care and/or provide timely coaching and behavioral modification cues.

Figure 2:
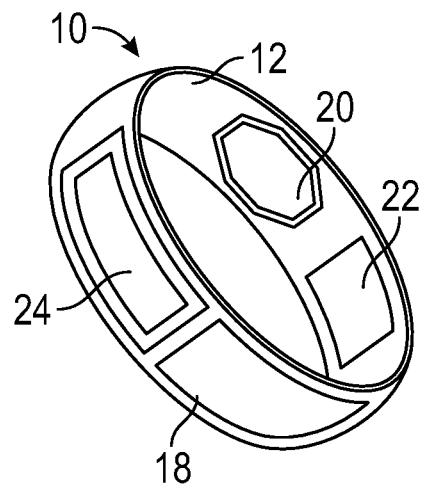
Figure 3:
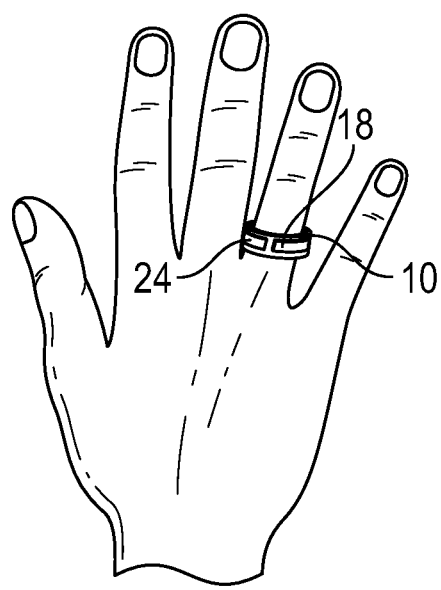
FIG. 3 shows the ring of FIGS. 1 and 2 worn on a person's finger.

FIGS. 1 and 2 illustrate one exemplary wearable ring 10 according the disclosed technology. The ring 10 includes an annular frame or body 12 having an inner surface that faces the skin of the finger and an outer surface facing away from the finger, an inner electrode 14 on the inner surface, a palmar electrode 16 on the outer surface, a dorsal electrode 18 on the outer surface, a pulse oximetry sensor 20, a galvanic skin sensor 22, and a button 24 that can be pressed to activate various functions of the ring, such as initiating an algorithms or synching the ring to a computing device via Bluetooth or other wireless means. FIG. 3 shows the ring 10 worn on a patient's finger with the dorsal electrode 18 at the back side of the hand and the palmar electrode 16 at the palm side of the hand.

Figure 4:
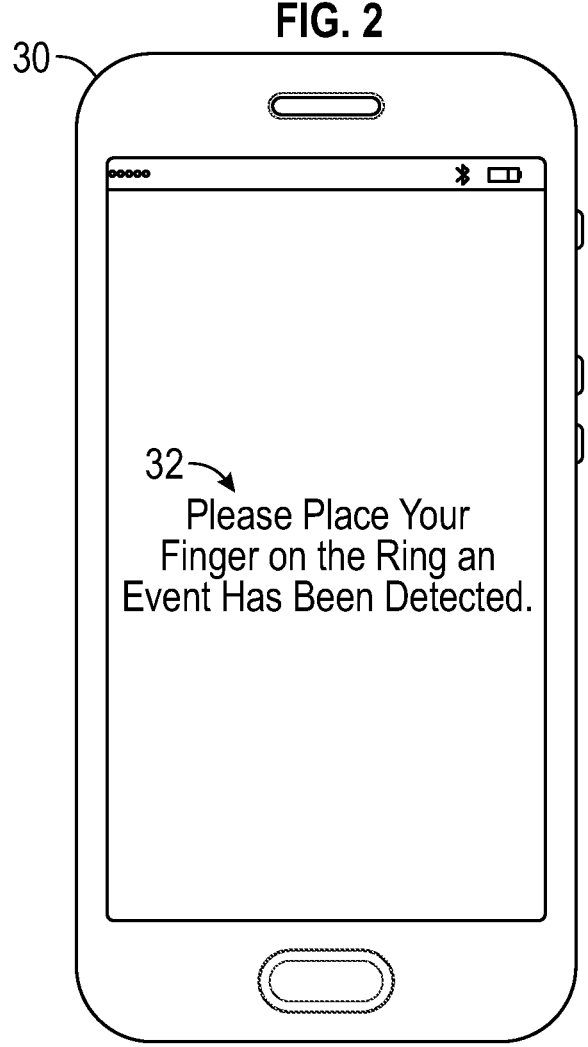
FIG. 4 shows a mobile computing device that can be linked with disclosed wearable devices to provide interaction with the wearer, provide computational and storage services, and/or communicate with other entities.

FIG. 4 shows an exemplary mobile computing device 30 (e.g., smart phone, tablet, etc.) that can be linked to the ring 10 via wireless communication means and can be used by the patients or another person to interact with the system. The device 30 can include interface devices such as a display that provides prompts or instructions 32 to the wearer. In FIG. 4, for example, the device 30 is prompting the wearer of the ring 10 to place a finger from the opposite hand on the dorsal electrode to initiate a diagnostic sequence, in response to a cardiovascular event having been possibly detected.

Figure 6:
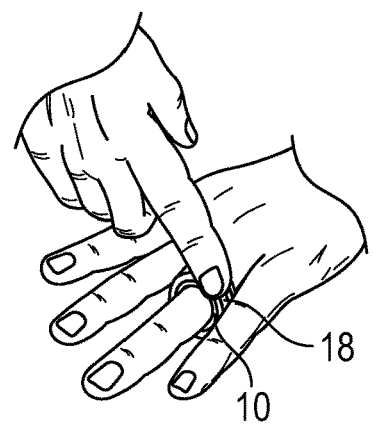
FIG. 6 shows a person with a ring on a finger touching a sensor of the ring with a finger of the other hand to measure cardiovascular properties of the wearer.

FIG. 6 shows the wearer placing a finger of the opposite hand on the dorsal electrode 18 of the ring 10 to carry out a two-electrode measurement/diagnostic process. In the position of FIG. 6, the inner electrode 14 is also touching the skin of the finger on which the ring is worn, but the palmar electrode 16 is not active.

Figure 5:
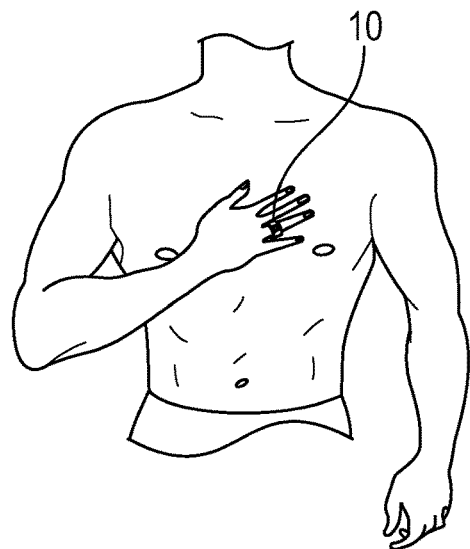
FIG. 5 shows a person with a ring on a finger touching a sensor of the ring to a lead location on the chest to measure cardiovascular properties of the wearer.
Figure 7:
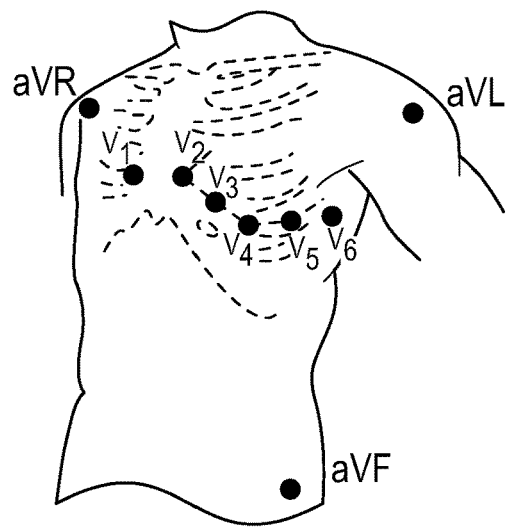
FIG. 7 shows exemplary EKG lead locations on the human anatomy.

FIG. 5 shows another position wherein the person wearing the ring 10 places the palmar electrode 16 of the ring 10 against his chest, for example at a precordial lead location. In this position, the inner electrode 14 is also touching the skin of the finger on which the ring is worn, but the dorsal electrode 16 is not active. The positions of FIGS. 5 and 6 can be combined in a position wherein the palmar electrode 16 is touching the patient's chest/leg/other body part and the patient has one or more fingers from the opposite hand touching the dorsal electrode 16, such that all three electrodes 14, 16, 18 are in contact with different parts of the patient's body can be used simultaneously. Depending on the purpose and/or what part of the body the palmar electrode 16 is touching, the three electrodes 14, 16, 18 can be controlled and utilized in different combinations and manners, including switching the polarity of each electrode as needed for various measurement/diagnostic purposes. FIG. 7 shows the locations of several EKG lead locations to which the palmar electrode 16 can be touched to measure specific EKG lead data. A full 12 lead EKG data set can be determined from as few as four or five precordial lead readings, for example.

Figure 8:
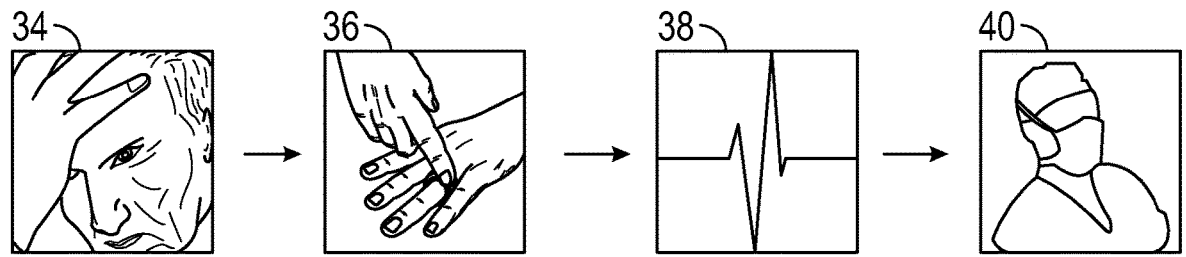
FIG. 8 is a flow chart illustrating an exemplary method wherein a person experiences symptoms, initiates cardiovascular measurement using the worn ring, and the data is transmitted to a health care provider for interpretation.

FIG. 8 shows an exemplary user-initiated method wherein a person notices symptoms at 34, the user initiates a measurement process by touching the dorsal electrode 18 with a finger at 36, the ring 10 measures and collects data at 38, and the data is sent to a healthcare provider for analysis and interpretation at 40. The healthcare provider can then determine appropriate subsequent actions, such as further testing, emergency care, etc.

Figure 9:
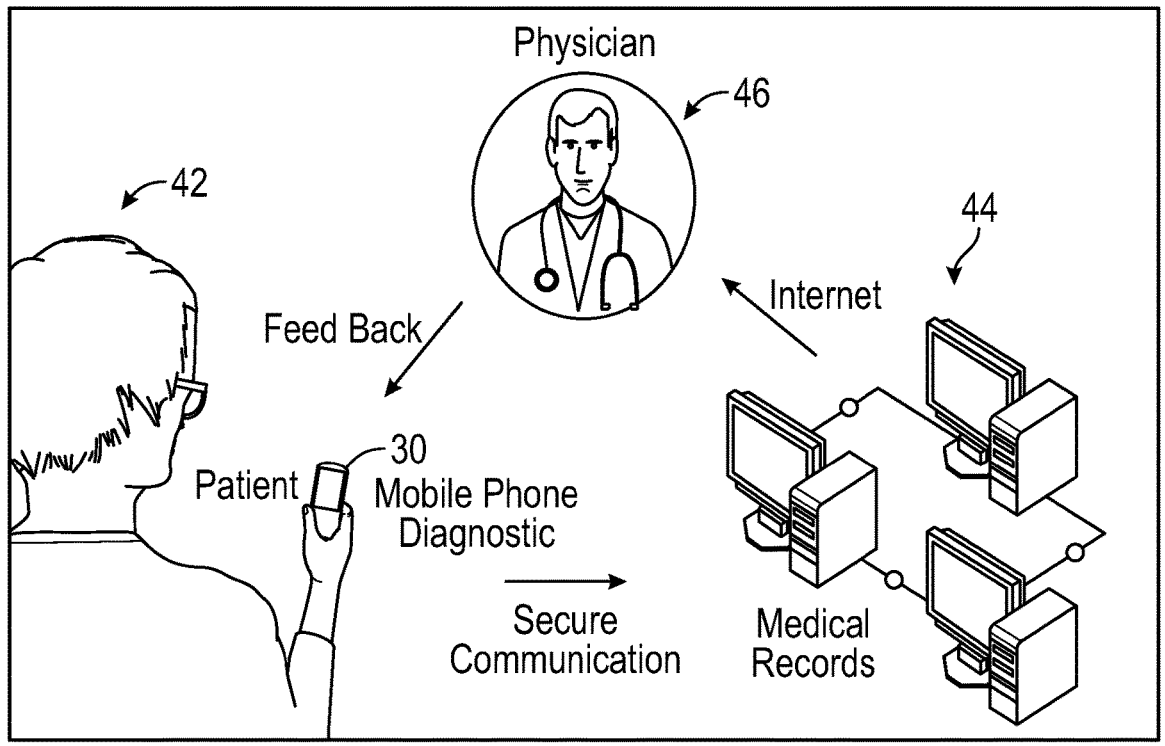
FIG. 9 shows an exemplary distributed system including a patient with a wearable device and a connected mobile computing device, a medical records database, and a health care provider, all in communication with one another.

FIG. 9 shows an exemplary distributed system that includes the patient 42 wearing the ring 10 or other disclosed wearable device and utilizing a smart phone to communicated data to and from a medical records database or other information source/server 44 and a physician or other healthcare provider 46. The healthcare provider 46 can interpret the data generated by the wearable device along with other patient data and non-patient information and instruct the patient accordingly.

Figure 10:
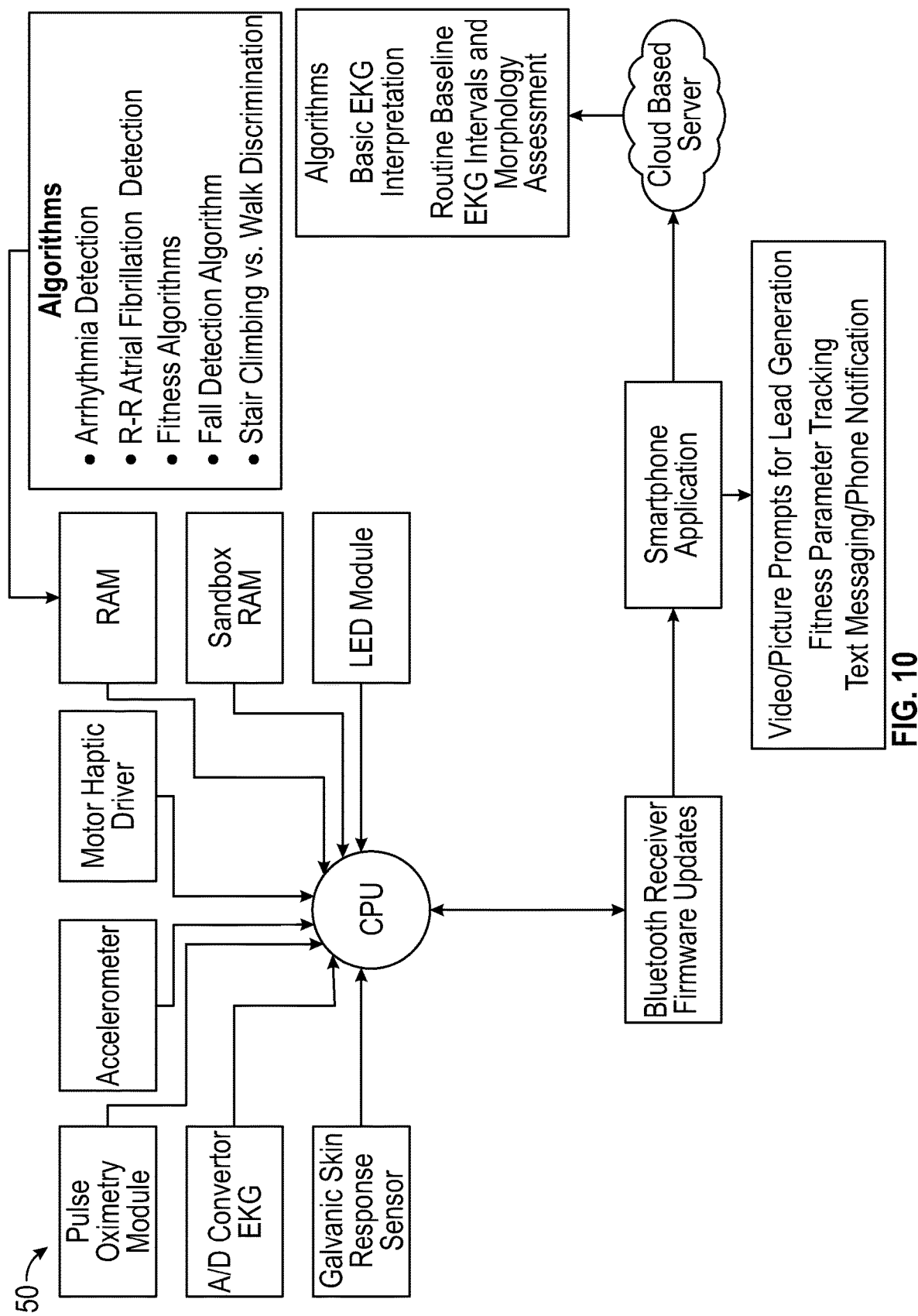
FIG. 10 shows an exemplary distributed system including a wearable device, a mobile computing device, and a cloud based server system.

FIG. 10 provides a schematic diagram of an exemplary distributed system 50 that includes a wearable device, a smartphone, and a cloud based server. The wearable device in the system 50 can include various components, such as a central processing unit (CPU), a galvanic skin response sensor, an analog to digital EKG convertor, a pulse oximetry module, an accelerometer, a haptic driver motor, RAM storing various algorithms (such as for arrhythmia detection, R-R atrial fibrillation detection, fitness algorithms, fall detection algorithms, and/or stair climbing vs. walk discrimination), sandbox RAM, an LED module, firmware, and/or a Bluetooth receiver (or other wireless communication means). The smartphone of the system 50 can include related applications, such as for fitness parameter tracking, text messaging and phone notification, and video/audio/haptic prompts for actions (e.g., EKG lead generation). The cloud based server of the system 50 can include various applications and data storage, and can carry out various methods, such as EKG interpretation, routine baseline EKG intervals and morphology assessment, etc.

Figure 11:
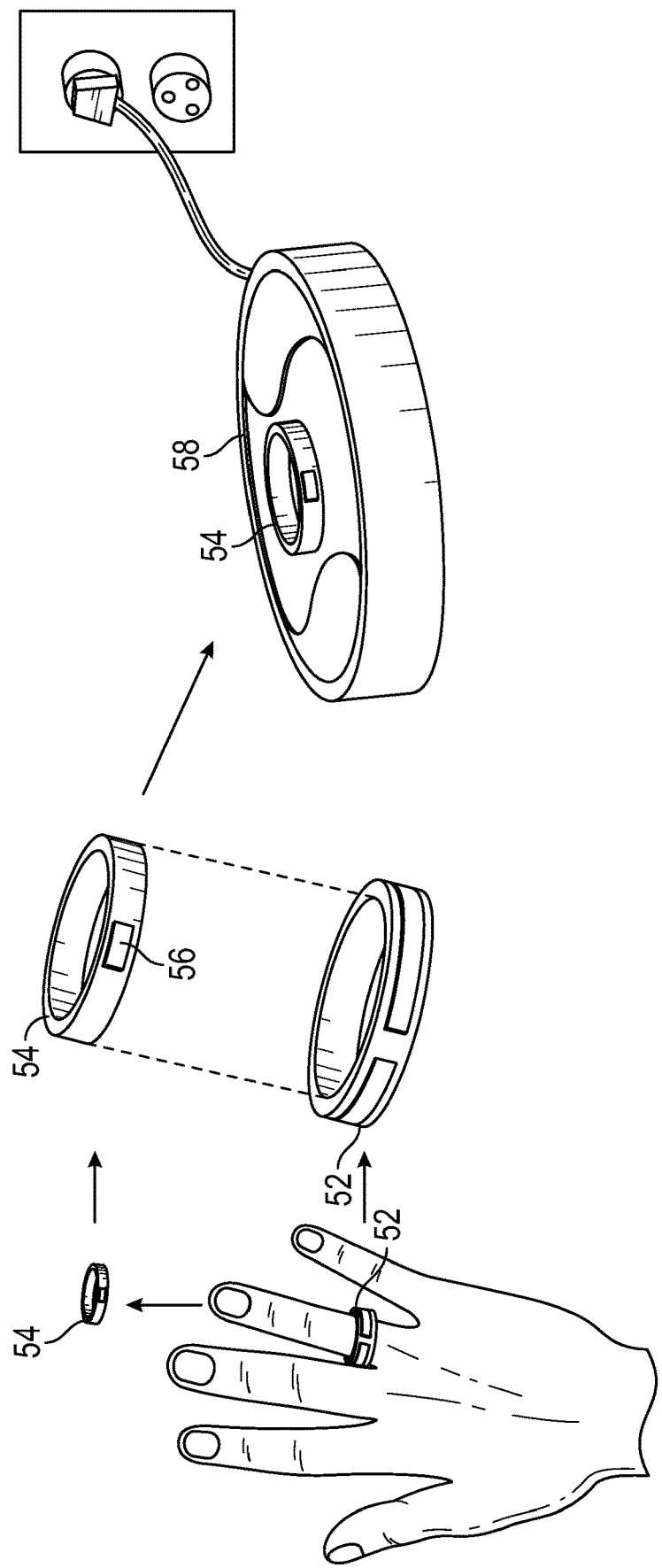
FIG. 11 shows an exemplary wearable ring that includes a detachable battery component that can be recharged using a wireless recharging station.
Figure 12:
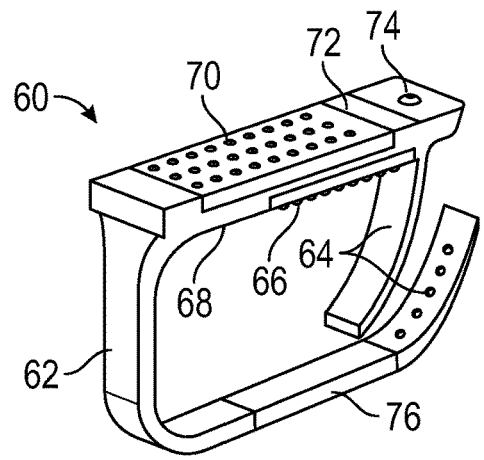
FIGS. 12-15 show an exemplary wearable bracelet that includes sensors and other technology for measuring physiological properties of the wearer to monitor and/or diagnose cardiovascular health conditions.
Figure 13:
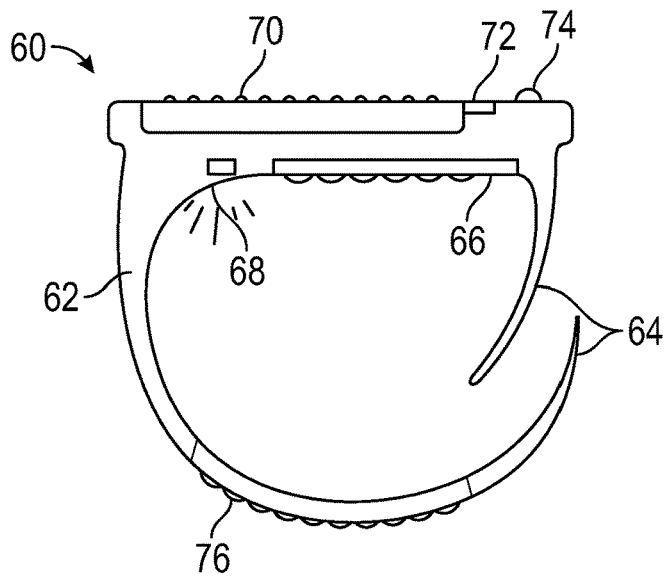
Figure 14:
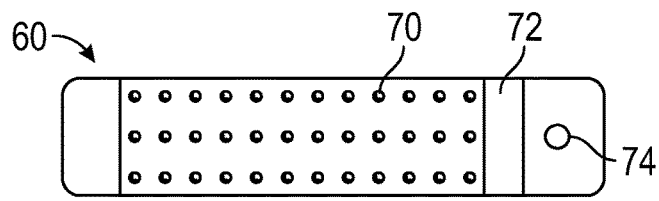
Figure 15:
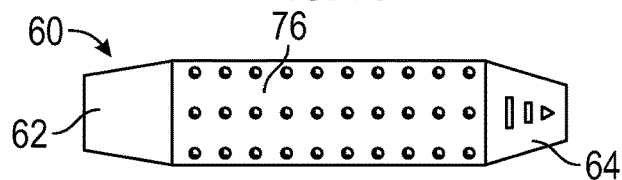

FIG. 11 illustrates an exemplary wearable ring device that includes a main ring portion 52 (similar to the ring 10 described herein) and a detachable battery portion 54. For example, the batter portion 54 can include an indicator 56 to show when it is running low on power and needs to be recharged. The battery portion 54 can be detached from the main portion 52 can recharged by placing the battery portion in proximity to a wireless recharging station 58, for example. The main portion 52 can include a secondary power supply, so that the device can remain continuously active even when the detachable battery portion 54 is detached and being recharged. Analogous embodiments of wearable bracelets and other wearable devices can similarly include detachable and rechargeable battery portions.

Figure 18:
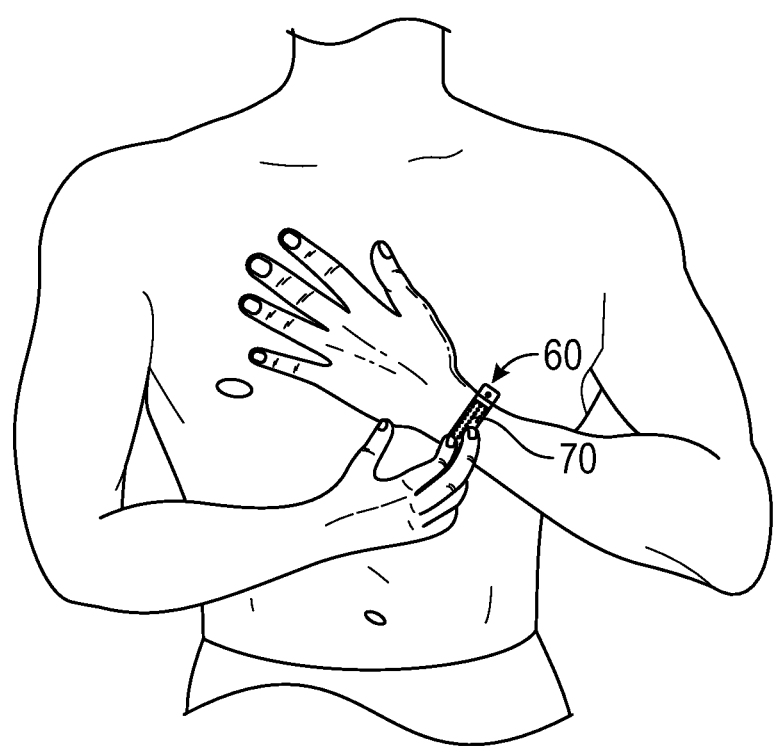
FIG. 18 shows a person wearing the bracelet of FIG. 12 touching a sensor of the bracelet to an EKG lead location on the chest and simultaneously touching another sensor of the bracelet with the opposite hand.

FIGS. 12-15 illustrate an exemplary wearable bracelet 60 that can be worn on a patient's wrist (or as a band at other locations such as the arm, ankle, or leg) and that is similar to the ring 10 in function. The bracelet 60 comprises an annular frame or body 62 (e.g., TPU, hypoallergenic rubber, or other flexible material) having an inner surface that faces the skin of the wrist and an outer surface facing away from the wrist, an inner electrode 66 on the inner surface, a dorsal electrode 70 on the outer surface (FIG. 14), a palmar/ventral electrode 76 (FIG. 15) on the outer surface, a pulse oximetry sensor and/or a galvanic skin sensor 68 on the inner surface, a display 72, and a button 74 that can be pressed to activate various functions of the bracelet, such as initiating an algorithms or synching the bracelet to a computing device via Bluetooth or other wireless means. The electrodes 66, 70, 76 can include copper/gold/platinum plating or other surface material of high electrical conductivity. The electrodes can also include small bumps or teeth to improve electrical signal detection. The bracelet 60 can include an adjustable clasp 64 to secure snuggly it around the wrist and ensure the inner electrode 66 and sensors 68 are adjacent to the skin. FIG. 18 shows the bracelet worn on a patient's wrist with the dorsal electrode 70 at the back side of the wrist and the ventral electrode 76 at the underside of the wrist.

FIG. 16 shows an exemplary user-initiated method wherein a person wearing the bracelet 60 notices symptoms at 80, the person initiates a measurement process by touching the dorsal electrode 70 with a finger at 82, the bracelet 60 measures and collects EKG and other data at 84, and the data is sent to a healthcare provider for analysis and interpretation at 86. The healthcare provider can then determine appropriate subsequent actions, such as further testing, emergency care, etc.

FIG. 17 shows an exemplary device-initiated method wherein the bracelet 60 (e.g., while continuously monitoring a wearer) determines that a cardiac event may have occurred at 88, the bracelet communicates to a mobile device that displays instructions to the wearer to initiate diagnostic actions at 90, the wearer initiates a measurement process by touching the dorsal electrode 70 with a finger at 92, the bracelet 60 measures and collects EKG and other data and transmits the data to the smart phone at 94, and the data is sent to a healthcare provider or other analyst for analysis and interpretation at 96. A healthcare provider can then determine appropriate subsequent actions at 98, such as further testing, emergency care, change is lifestyle, etc.

FIG. 18 shows the wearer placing the ventral electrode 76 against an EKG lead location on his chest while simultaneously touching the dorsal electrode 70 with his fingers. This position can be part of an EKG data collection method wherein the patient repeats a similar actions while touching the ventral electrode to various different EKG lead locations on his body. Depending on the purpose and/or what part of the body the ventral electrode 76 is touching, the three electrodes 66, 70, 76 can be controlled and utilized in different combinations and manners, including switching the polarity of each electrode as needed for various measurement/diagnostic purposes. FIG. 7 shows the locations of several EKG lead locations to which the ventral electrode 76 can be touched to measure specific EKG data.

Figure 19:
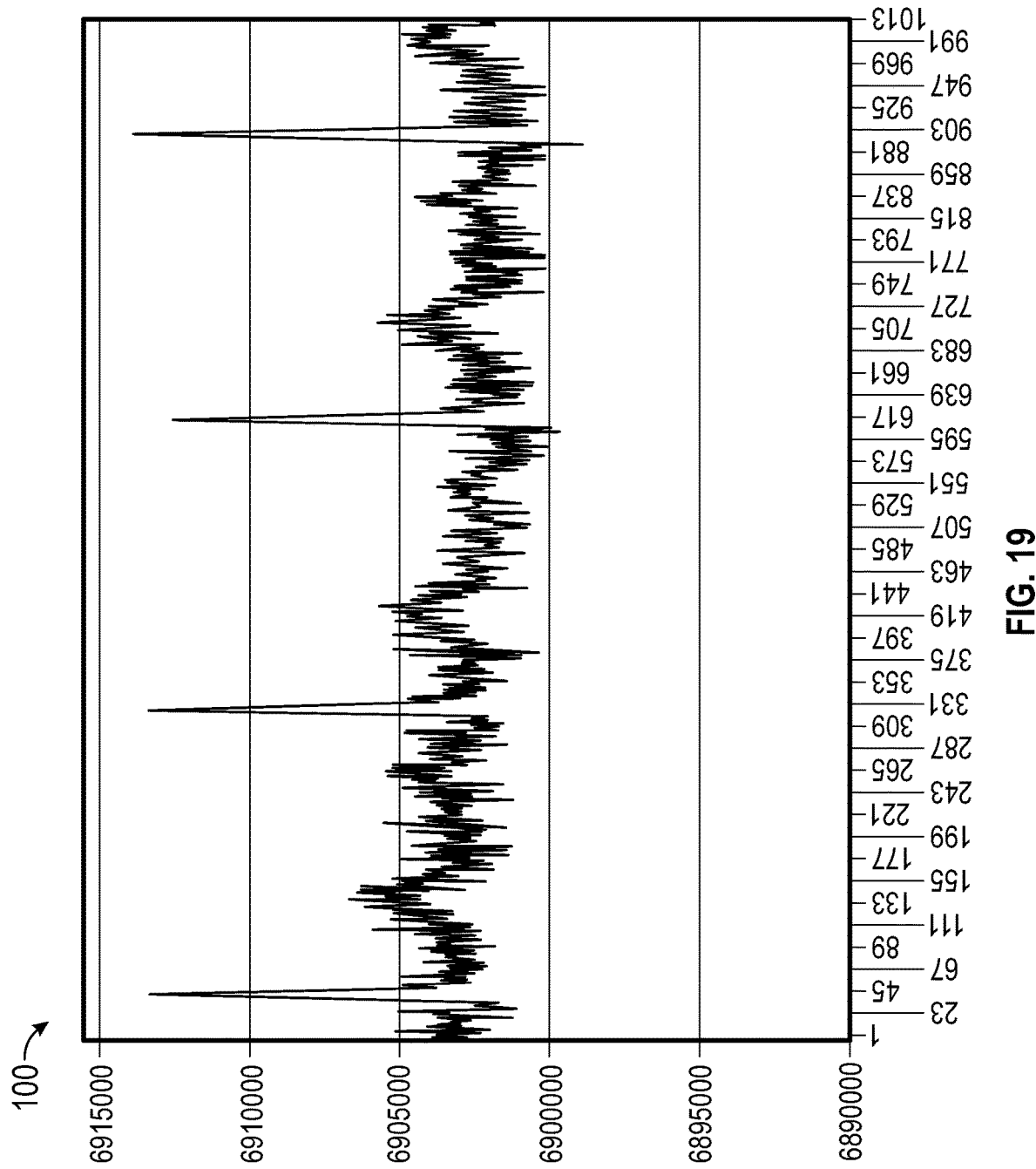
FIG. 19 shows an exemplary chart plotting heart rate data collected by a wearable device.
Figure 20:
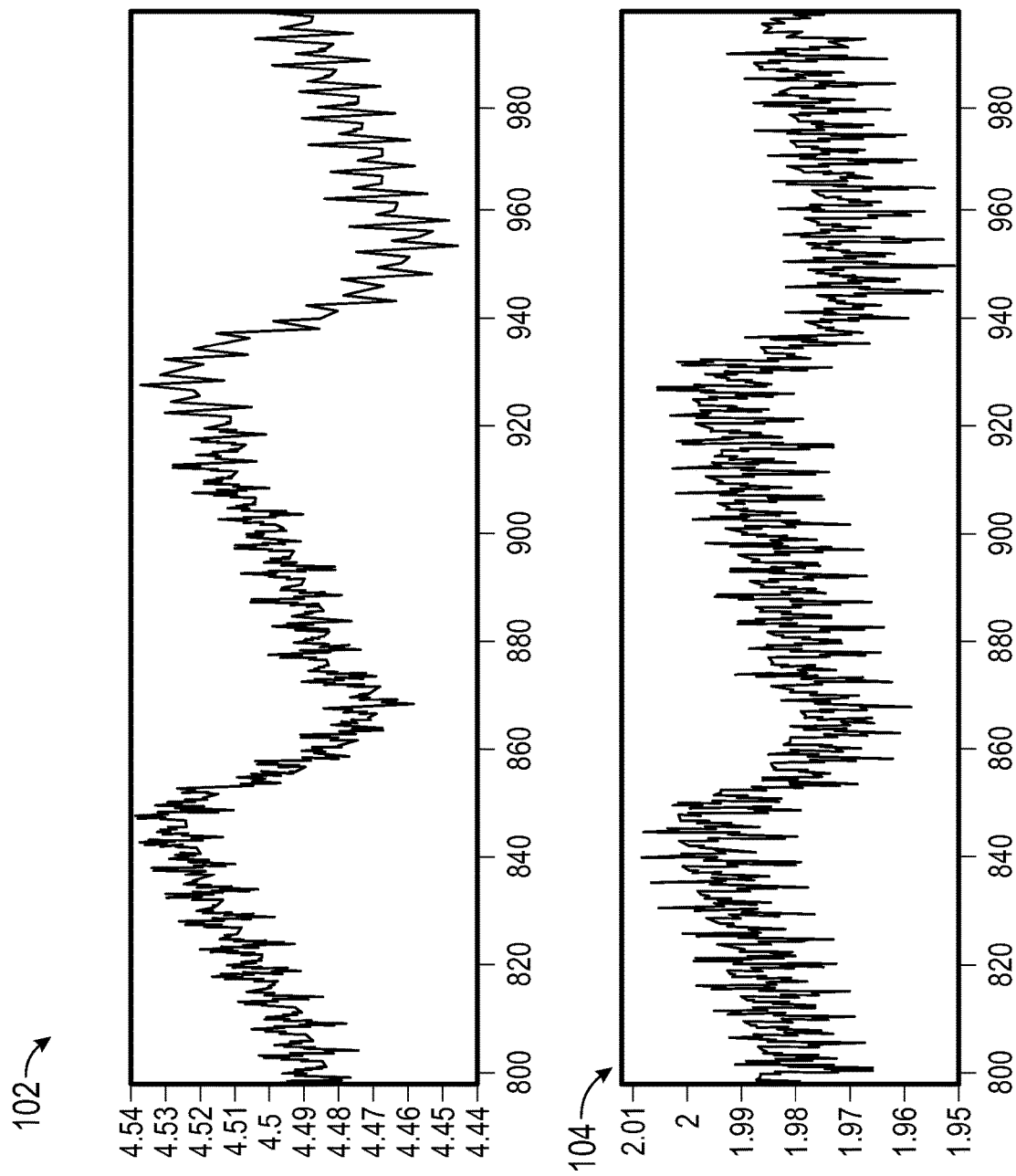
FIG. 20 shows exemplary charts plotting oxygen saturation data collected by a wearable device.

FIG. 19 is a chart showing exemplary EKG data that can be measured and utilized by the disclosed wearable devices. FIG. 20 includes two charts showing exemplary pulse oximetry data that can be measured and utilized by the disclosed wearable devices. The disclosed device can be capable of measuring EKG and pulse oximetry data at a high level of precision that is sufficient for interpretation using various interpretation techniques and/or at least as precise as data typically obtained by EKG equipment used in a hospital, emergency facility, or by emergency personnel outside of a medical facility.

Figure 21:
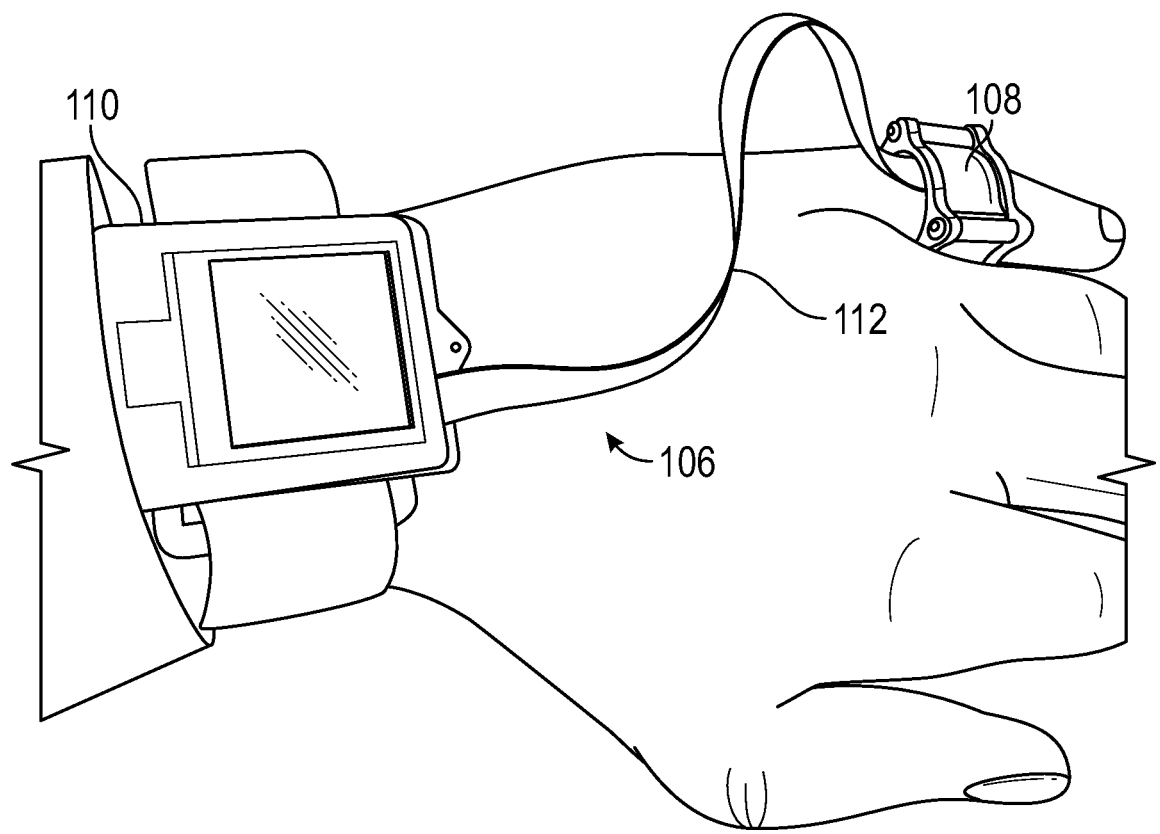
FIG. 21 shows an exemplary system comprising a bracelet and a ring worn on the same hand and linked together.
Figure 22:
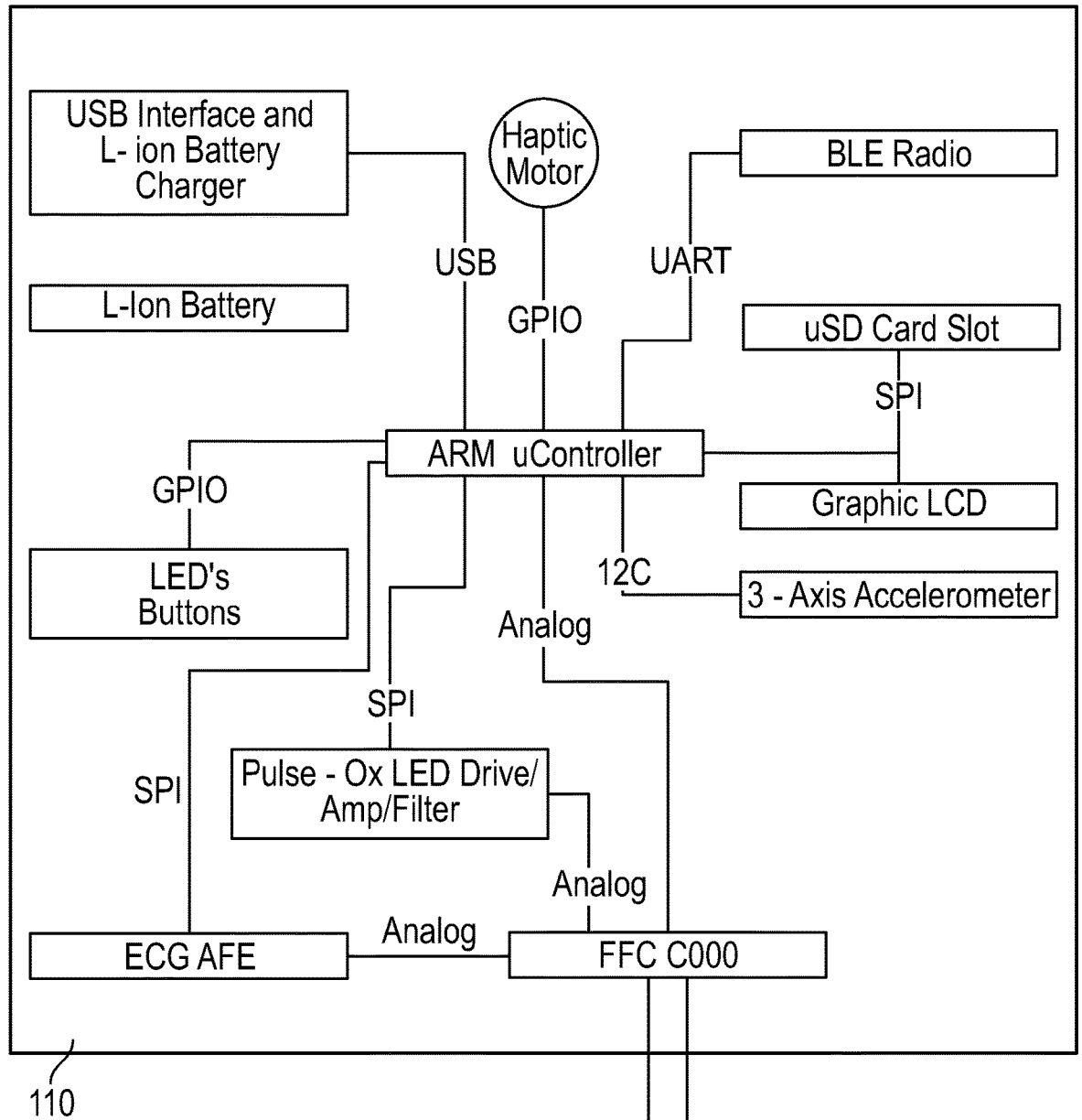
FIG. 22 is a diagram illustrating exemplary hardware components of the system of FIG. 21.
Figure 23:
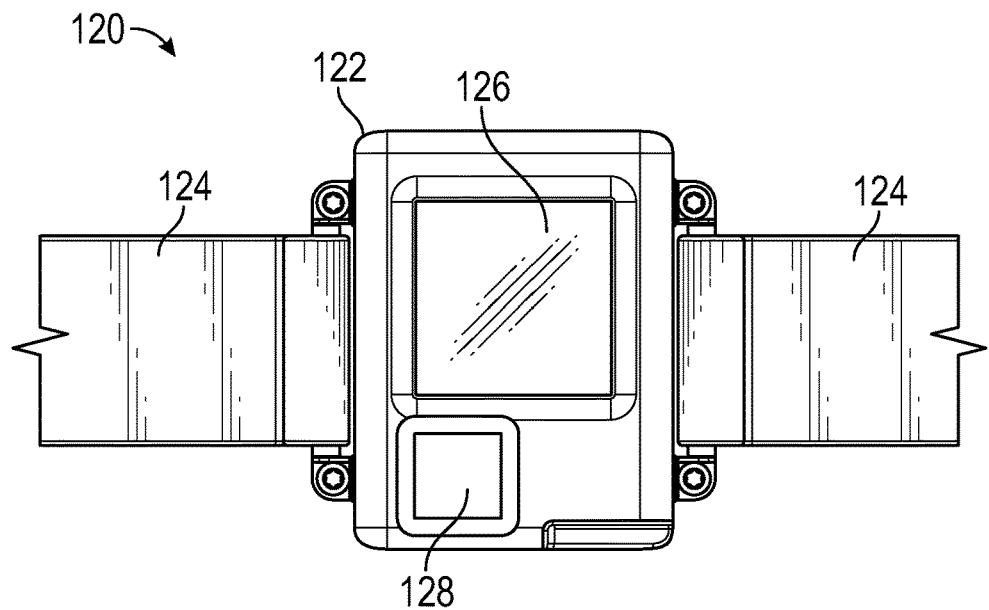
FIGS. 23-27 are various view of an exemplary wearable bracelet that includes sensors and other technology for measuring physiological properties of the wearer to monitor and/or diagnose cardiovascular health conditions.
Figure 24:
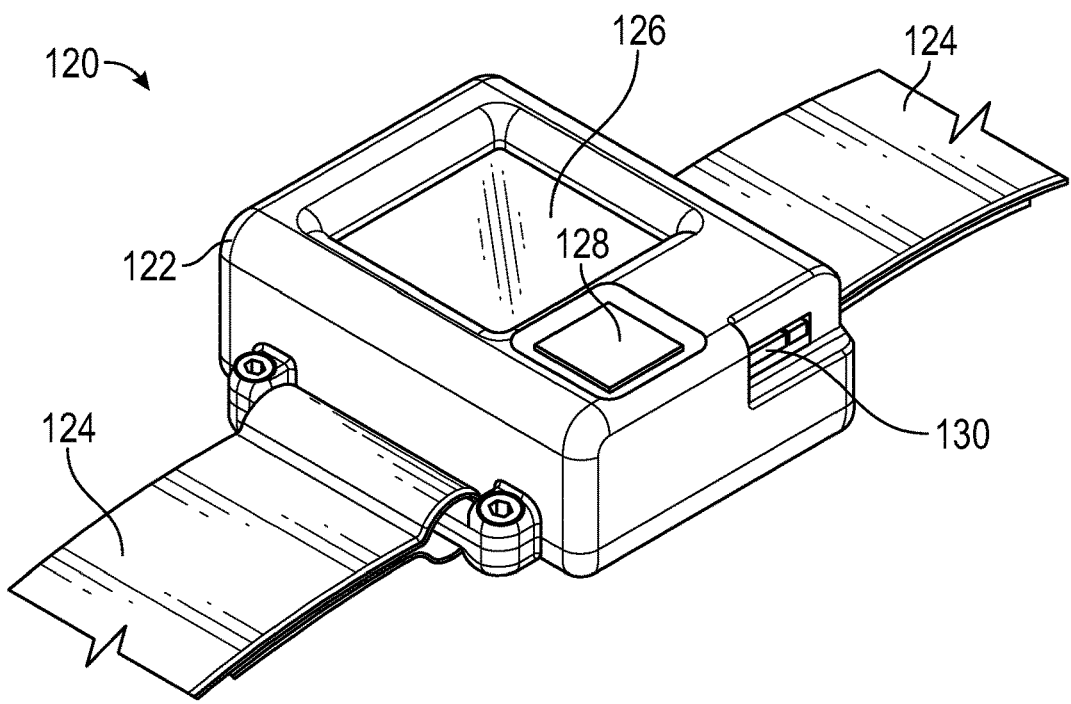
Figure 25:
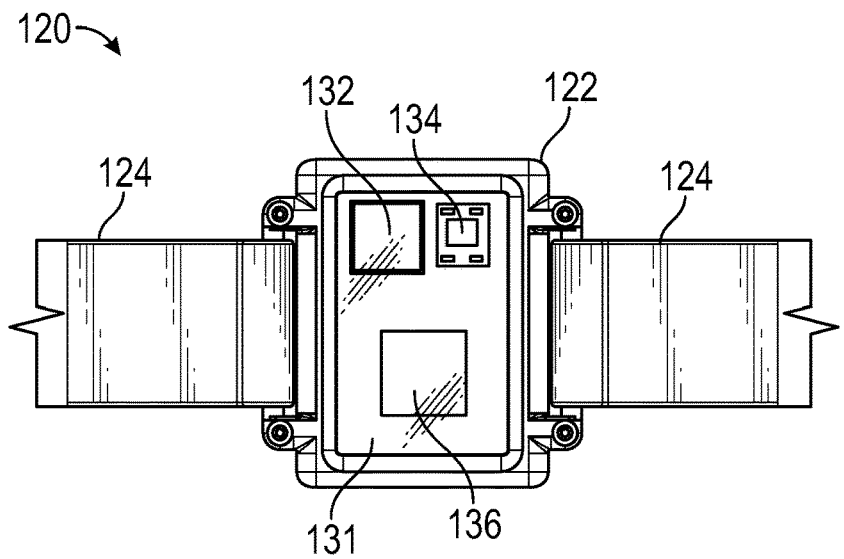
Figure 26:
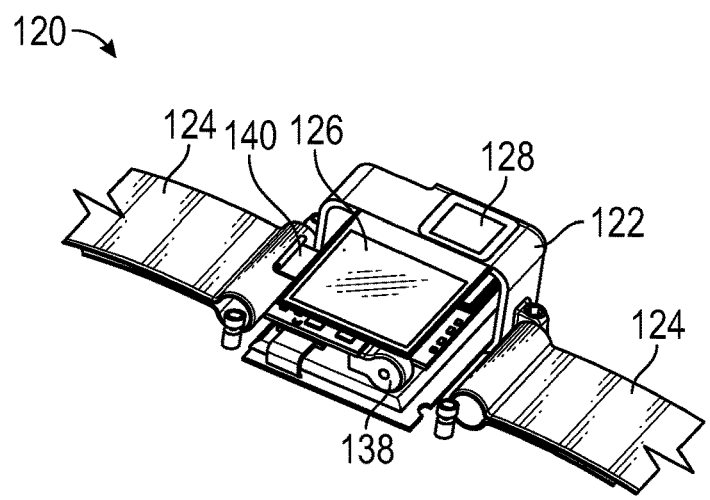
Figure 27:
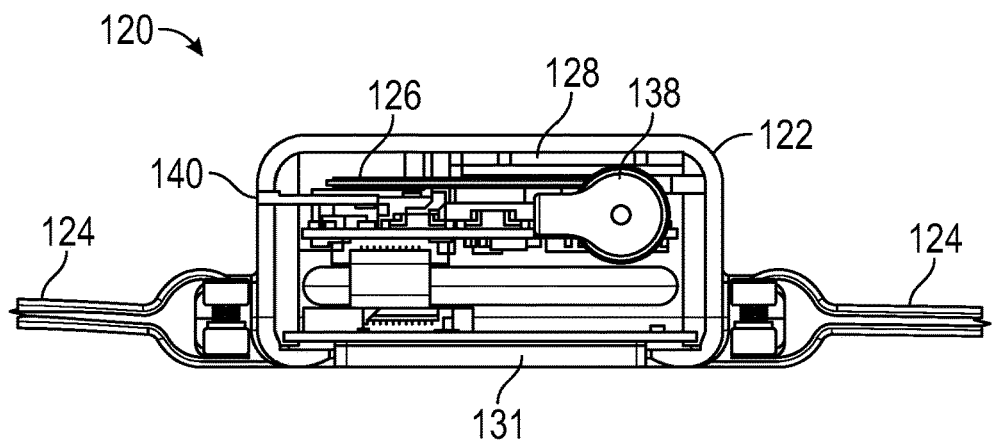

FIGS. 21 and 22 illustrate an exemplary system 106 that includes both a wearable ring 108 and a wearable bracelet 110. The ring and bracelet can be linkable via wireless communication and/or linkable via wired connection 112 as shown. In such a system, the ring 108 can be made more compact and comfortable as the ring 108 can include fewer components compared to the ring 10 disclosed herein. Some of the hardware components can be relocated from the ring to the bracelet 110, such as computing, storage, power source, and/or communication components. The ring 108 can still include some component, such as one or more electrodes (e.g., an inner electrode and/or one or two outer electrodes, and optionally a pulse oximetry sensor and/or a galvanic skin sensor). The bracelet 110 can include any of the components disclosed herein in relation to the ring 10 or bracelet 60, for example. The ring and bracelet can operate together to carry out any of the various functions and methods disclosed herein.

FIGS. 23-27 illustrate another exemplary bracelet 120 that can function similar to either of the bracelets 60 and 110 disclosed herein. The bracelet 120 includes a frame 122 coupled to straps 124 for securing around the wrist or arm. The frame 122 can house various components, including a display 126, button 128 for initiating action and/or synching to a mobile device or a ring, a I/O port 130 for wired connection to other devices such as a ring or battery charger, an inner panel 131 that faces the skin of the wrist and includes various sensors/electrodes 132/134/136 (e.g., EKG electrode, pulse oximetry sensor, galvanic skin sensor, etc.), a battery 138, a removable memory/storage device 140, a processor, wireless communication device, and/or various other mechanical/electronic/computing devices. The bracelet 120 may lack one or both of the outer electrodes of the bracelet 60, and instead a paired ring can include such electrodes. In use, a wearer may touch their ringer to an outer dorsal electrode on either the bracelet 120 or a paired ring. Similarly, the wearer may touch a palmar electrode on a paired ring to EKG lead locations rather than using an electrode on the bracelet for that purpose. A paired ring can be charged via wired connection to the I/O port on the bracelet, by wireless charging, or other means.

Figure 28:
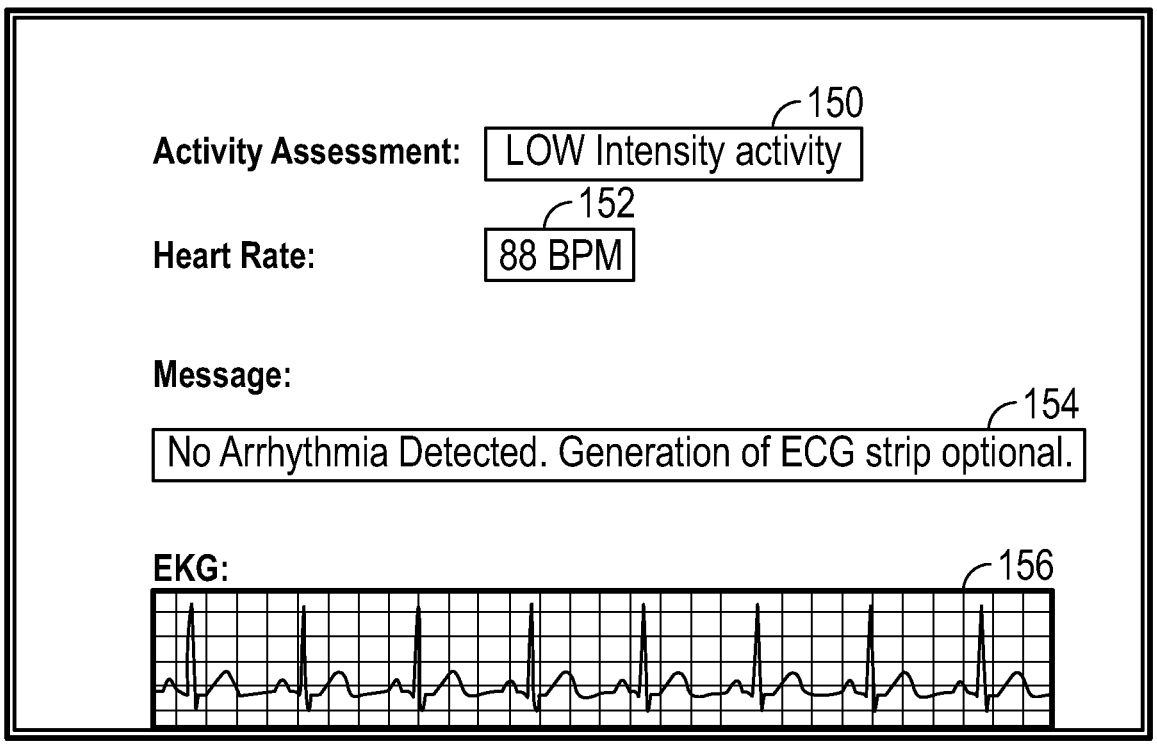
FIG. 28 shows an exemplary user interface related to a diagnostic algorithm based on measurements of a wearer's activity and heart rate.

FIG. 28 shows an exemplary user interface, such as can be displayed on a paired mobile computing device or a healthcare providers computer, which indicates an activity assessment 150, a heart rate assessment 152, an EKG waveform readout 156, and a resulting message 154 that include a diagnosis, prompt for further actions, recommendations for activity modifications, etc.

Figure 29:
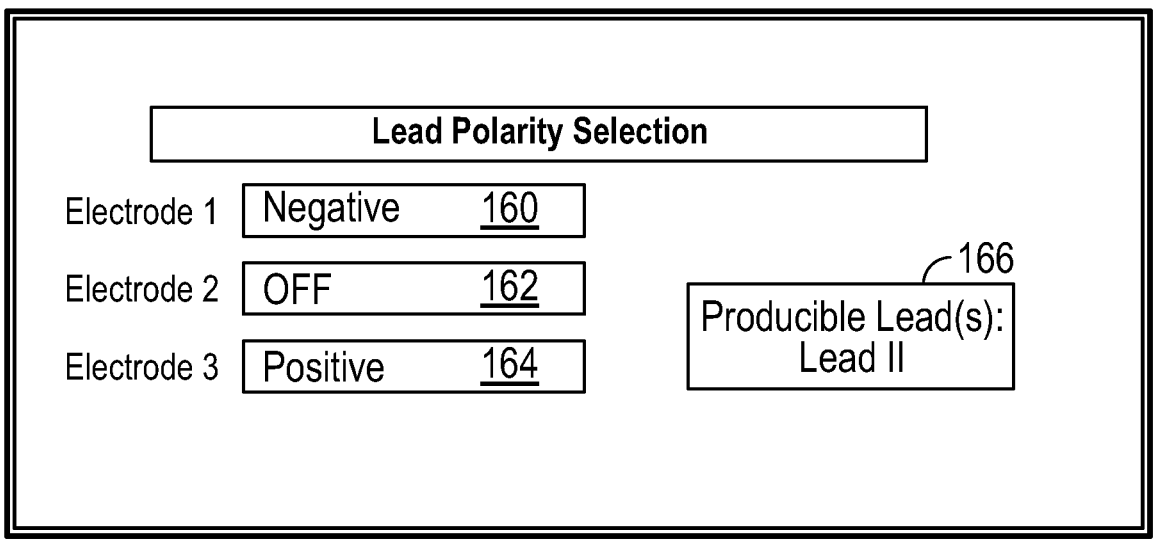
FIG. 29 shows another exemplary user interface related to a diagnostic algorithm based on EKG lead measurements taken using a worn device.

FIG. 29 shows another exemplary user interface, such as can be displayed on a paired mobile computing device or a healthcare providers computer, which indicates a first electrode status 160, a second electrode status 162, a third electrode status 164, and a list of producible leads 166 based on the electrode statuses 160/162/164. The list 164 can indicated which EKG leads can be produced using the wearable device with the three electrodes in the current polarity status. In the illustrated example, electrode 1 has a negative polarity, electrode 2 is off, and electrode 3 has a positive polarity. In this configuration, the wearable device can be used to produce EKG lead II. By adjusting the polarity status of the three electrodes of the wearable device, all 12 of the conventional EKG leads can be produced by the wearer while touching the device to the different lead locations in sequence. The user interface can instruct the wearer wear on the body to place the palmar/ventral electrode for each EKG lead measurement, and the software of the device/smartphone can determine how to adjust the polarity status of each electrode for each EKG lead location.

FIGS. 30-38 are flow charts that illustrate various exemplary algorithms/methods that can be performed by the disclosed wearable devices, mobile computing devices, and/or other system components. The illustrated algorithms can be used to continuously monitor a patient to look for possible cardiac event and help predict or warn of possible future cardiac events before they occur so that the wearer can avoid the events, reduce the effects of the events, and/or seek health care or other help in a minimal amount of time. Cardiac events that can be predicted before they occur and/or sensed while or after they occur include arrhythmia, atrial fibrillation, coronary blockage, ischemia, infarction, tachycardia, bradycardia, stroke, etc.

Figure 30:
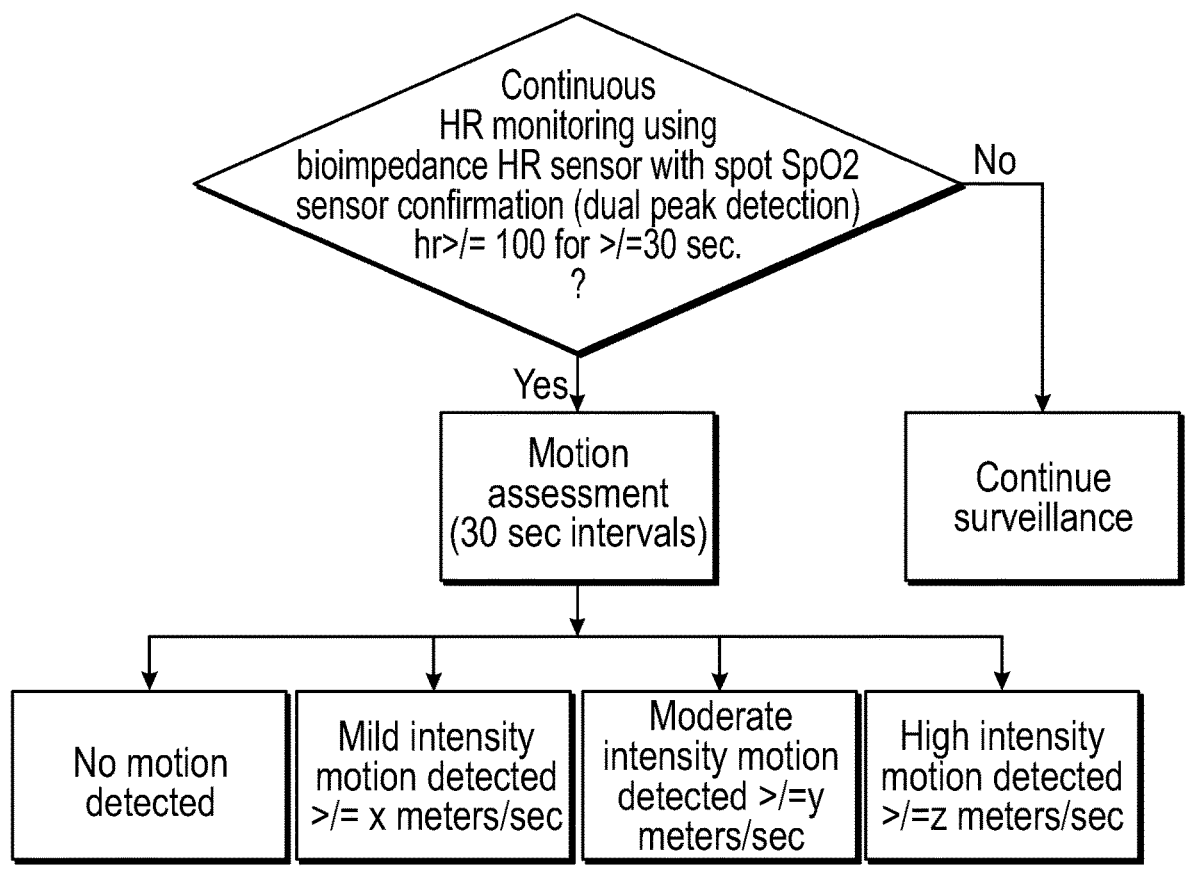
FIGS. 30-38 are flow charts illustrating exemplary diagnostic algorithms disclosed herein.

FIG. 30 illustrates a method wherein the wearable device continuously monitors the wearer's heart rate (e.g., using a bioimpedance heart rate sensor), with optional spot SPO2 sensor confirmation (e.g., dual peak detection), to determine if the heart rate is at least 100 bpm for at least 30 seconds. Different threshold values for the bpm and period can be used as appropriate. If the measured heart rate does not meet the threshold values, then the device/system can continue to monitor the wearer. If the measured heart rate does meet the threshold values, then motion assessment can be performed (e.g., in 30 second intervals). The motion assessment can be performed using sensors such as accelerometer, gyroscope, GPS, etc. The result of the motion assessment can be one of several threshold ranges, such as no motion, mild intensity (greater than X m/s but less than Y m/s), moderate intensity (at least Y m/s but less than Z m/s), or high intensity (at least Z m/s), as illustrated.

Figure 31:
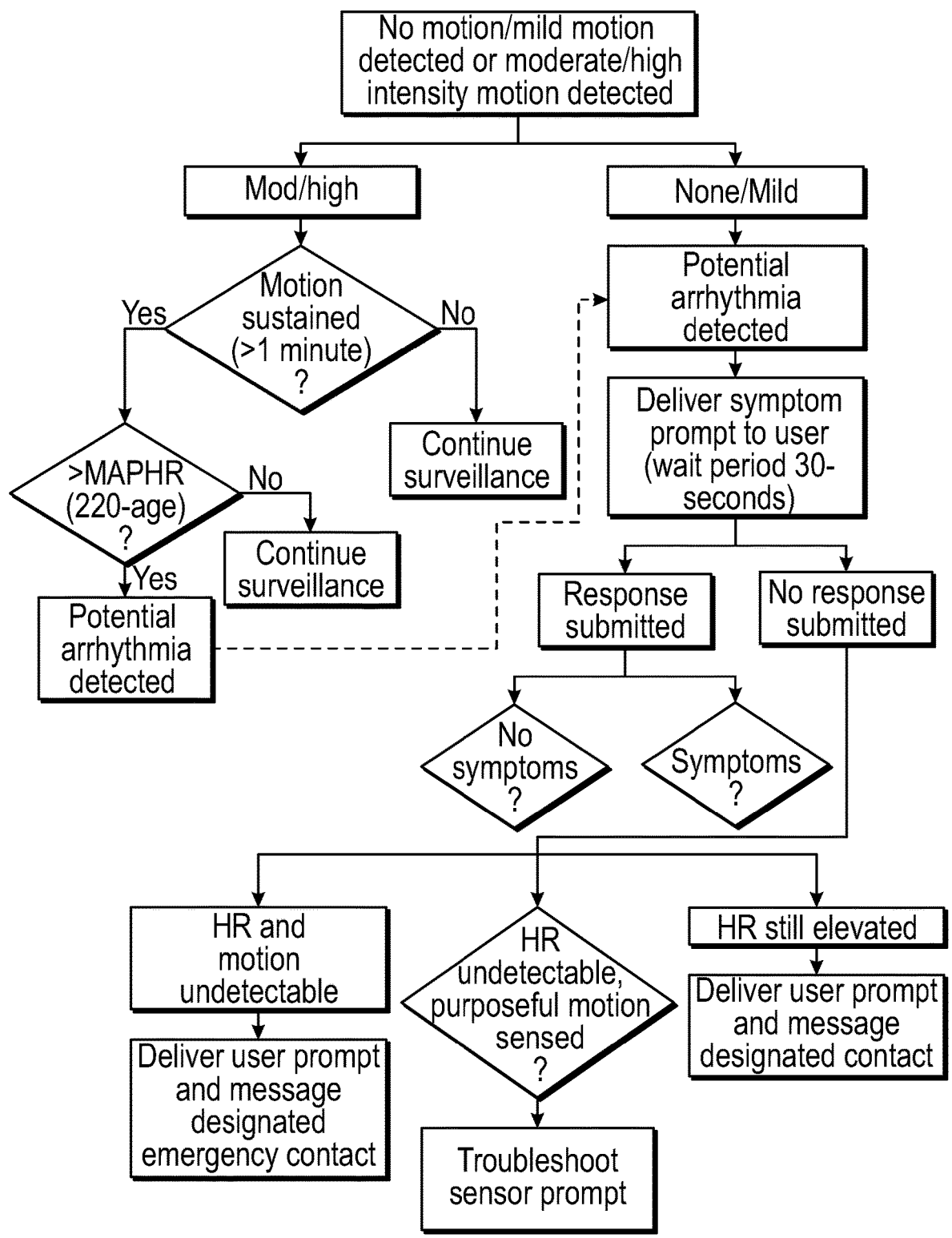

As illustrated in FIG. 31, if moderate or high intensity is detected, the method can check if the motion is sustained for a certain time, such as at least one minute. If not, the method can continue surveillance of the wearer. If the high/moderate motion is sustained, then the method can check if the wearer's heart rate exceeds their maximum age-predicted heart rate (MAPHR), e.g., greater than 220 minus their age in years. If the heart rate does not exceed the MAPHR, then the method can continue surveillance of the wearer. If the heart rate does exceed the MAPHR, then the method can determine that potential arrhythmia has been detected. Similarly, if the motion assessment results in no motion or mild motion while the heart rate is elevated, then the method can determine that potential arrhythmia has been detected. When potential arrhythmia is detected, the method can cause the system to deliver a prompt to the wearer (e.g., waiting for 30 seconds for the wearer to respond). If no response is submitted by the wearer, the method can check if the wearer's heart rate and motion are undetectable, and if so it can deliver a prompt and message a designated emergency contact. If the heart rate is undetectable and purposeful motion is sensed, then the method can cause a troubleshoot sensor prompt. If heart rate is still elevated, the method can deliver a prompt to the wearer and message a designated contact.

Figure 32:
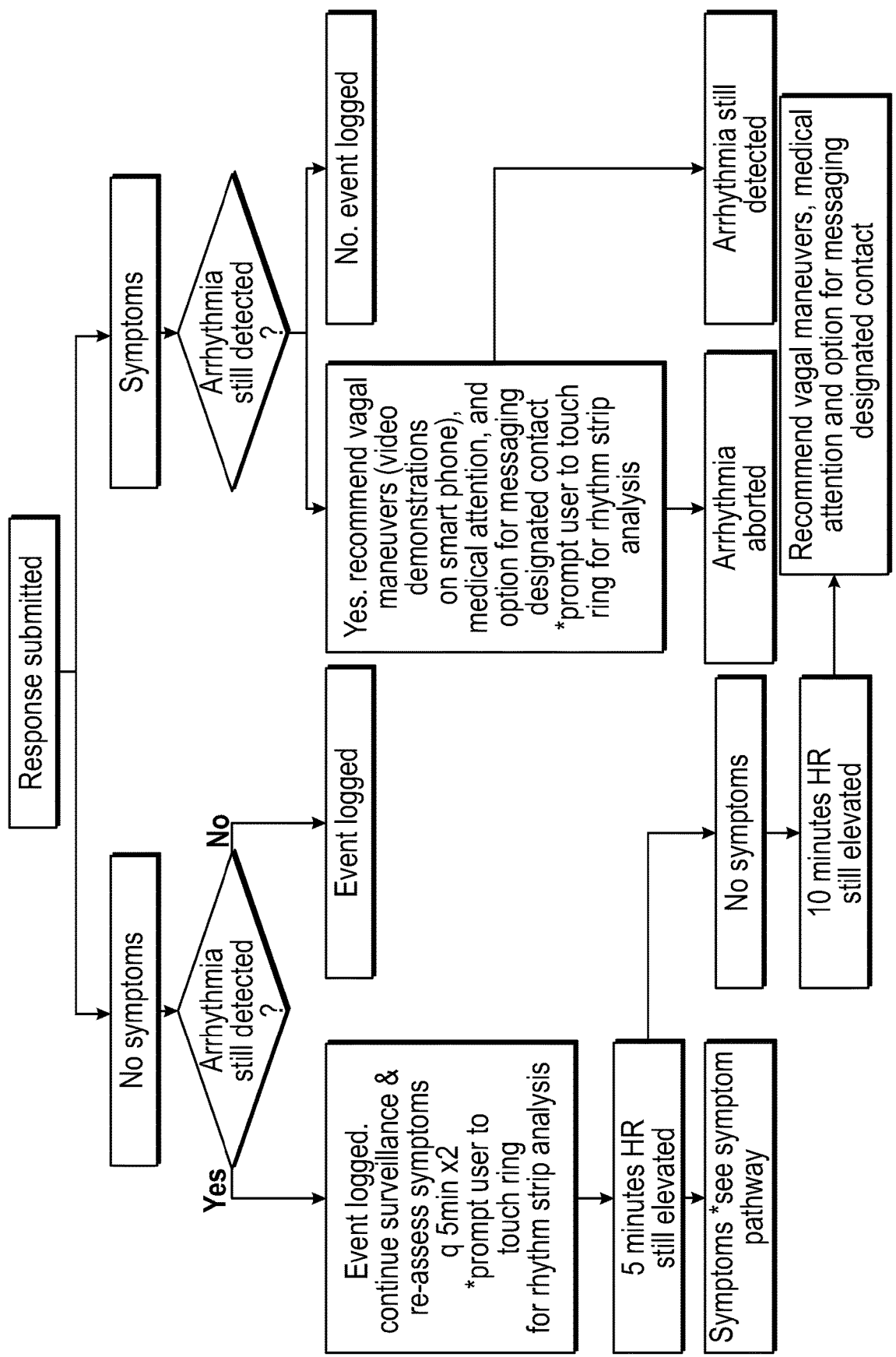

As illustrated in FIG. 32, if potential arrhythmia is detected and a response to the symptom prompt is submitted by the wearer indicating the wearer is experiencing symptoms, then the method can check if arrhythmia is still detected. If not, the event can be logged. If arrhythmia is still detected, then the method can log the event and continue surveillance and reassess symptoms every so often, such as every five minutes, for a certain number of times, such as two times. The method can also prompt the wearer to touch the wearable device to generate an EKG rhythm strip analysis. If after a period of time, such as five minutes, the wearer's heart rate is still elevated, if symptoms not reported, the method can wait another five period of time and check for symptoms again, and if the heart rate is still elevated after two periods of time, such as 10 minutes, the method can recommend vagal maneuvers, medical attention, and/or optionally messaging a designated contact. If symptoms are reported at any step after the potential arrhythmia is detected and the wearer is prompted for symptoms, the method can check if arrhythmia is still detected. If not, the event can be logged. If arrhythmia is still detected, then the method can recommend vagal maneuvers (e.g., with a video demonstration on a smartphone), medical attention, and/or optionally messaging a designated contact. The method can also prompt the wearer to touch the wearable device to generate EKG analysis.

Figures 33, 34:
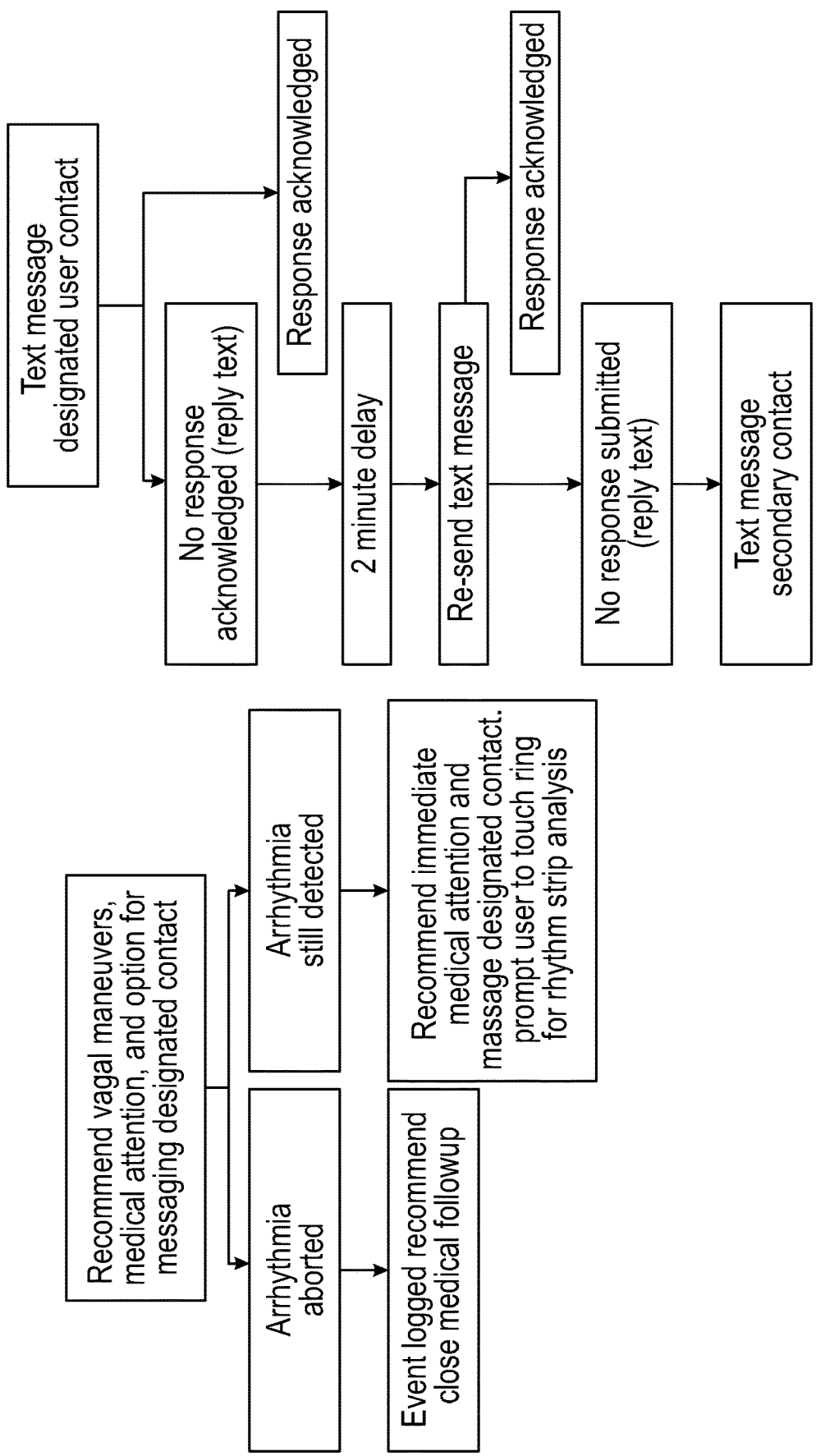

As illustrated in FIG. 33, after recommending vagal maneuvers, medical attention, and/or messaging a designated contact, the method can determine if the arrhythmia is aborted, in which case the event can be logged and close medical follow up can be recommended, or if arrhythmia is still detected, in which case the method can recommend immediate medical attention and message a designated contact. The method can continue to periodically prompt the wearer to touch the wearable device to generate EKG analysis.

As illustrated in FIG. 34, if a message is sent to a designated contact, and no response is acknowledged (e.g., by a reply text), then the method can wait for a period, such as two minutes, and re-send the message to the designated contact. If still no response is received, the method can cause a message to be sent to a secondary contact, and so on until a response is received.

Figure 35:
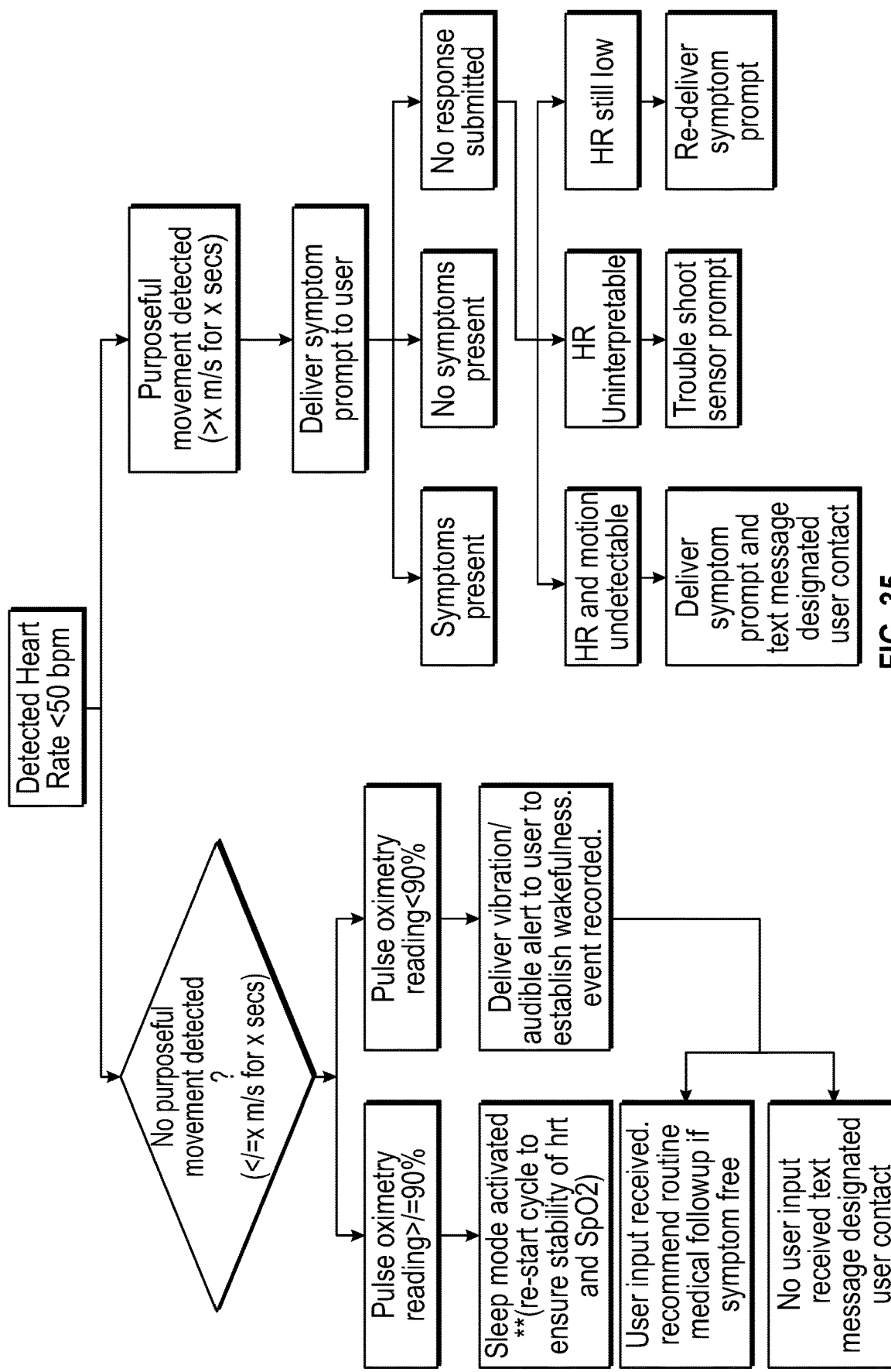

FIG. 35 illustrates a method wherein the wearable device continuously monitors the wearer's heart rate (e.g., using a bioimpedance heart rate sensor), with optional spot SPO2 sensor confirmation (e.g., dual peak detection), to determine if the heart rate is less than 50 bpm, optionally over a certain period. Different threshold values for the bpm and period can be used as appropriate. If the measured heart rate drops below the threshold value, then motion assessment can be performed (e.g., as described above with FIG. 30). If no purposeful movement is detected (e.g., less than X m/s for at least Y seconds), then the method can measure the wearer's blood oxygen level using pulse oximetry. If the oxygenation is at least 90%, the method can determined the wearer is likely asleep and active sleep mode, in which the method can continue surveillance of the wearer until motion is detected. If oxygenation is less than 90%, the method can deliver a vibratory and/or audible alert to the wearer to establish wakefulness, and record the event. If an input from the wearer is then received, the method can recommend routine medical follow-up if they wearer is symptom free. If no input is received from the wearer in response to the alert, the method can message a designated contact, such as 911.

If the method detects purposeful movement (e.g., at least X m/s for at least Y seconds), the method can deliver a symptom prompt to the wearer. If no response is submitted to the prompt, the method can check if the wearer's heart rate and motion are undetectable, and if so it can deliver a prompt to the wearer and message a designated emergency contact. If the heart rate is undetectable/uninterpretable, then the method can cause a troubleshoot sensor prompt. If the heart rate is still low, the method can re-deliver a symptom prompt to the wearer.

Figure 36:
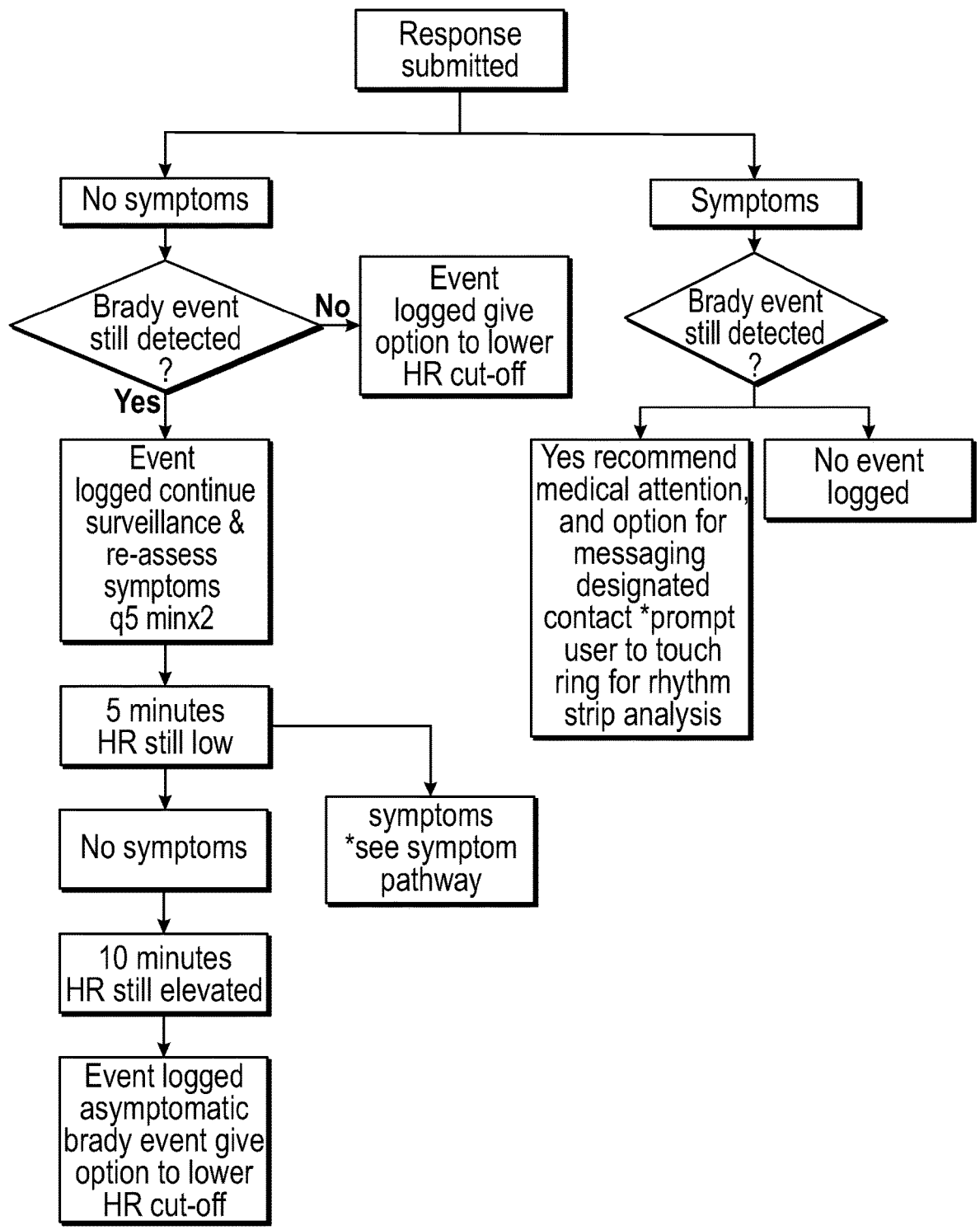

As illustrated in FIG. 36, if the heart rate is low, purposeful movement is detected, and the wearer responds to the symptom prompt that the wearer is experiencing symptoms, the method can check if a low heart rate event is still detected. If not, the event can be logged, and if so, then the method can recommend medical attention and optionally message a designated contact. If the wearer responds to the symptom prompt that no symptoms present, the method can check if a low heart rate event is still detected. If not, the event can be logged and the method can optionally provide the option of lowering the minimum heart rate threshold (such as from 50 bpm to a lower rate). If the heart rate is still low, the event can be logged and the method can continue surveillance and reassess for symptoms every five minutes, or other interval. If after 10 minutes, or other interval, if still no symptoms are detected and the heart rate is still low, the method can determine that an asymptomatic bradycardia event is likely occurring. In that case, the method can optionally message to a designated contact or medical personnel. The method can optionally provide the option of lowering the minimum heart rate threshold (such as from 50 bpm to a lower rate).

Figure 37:
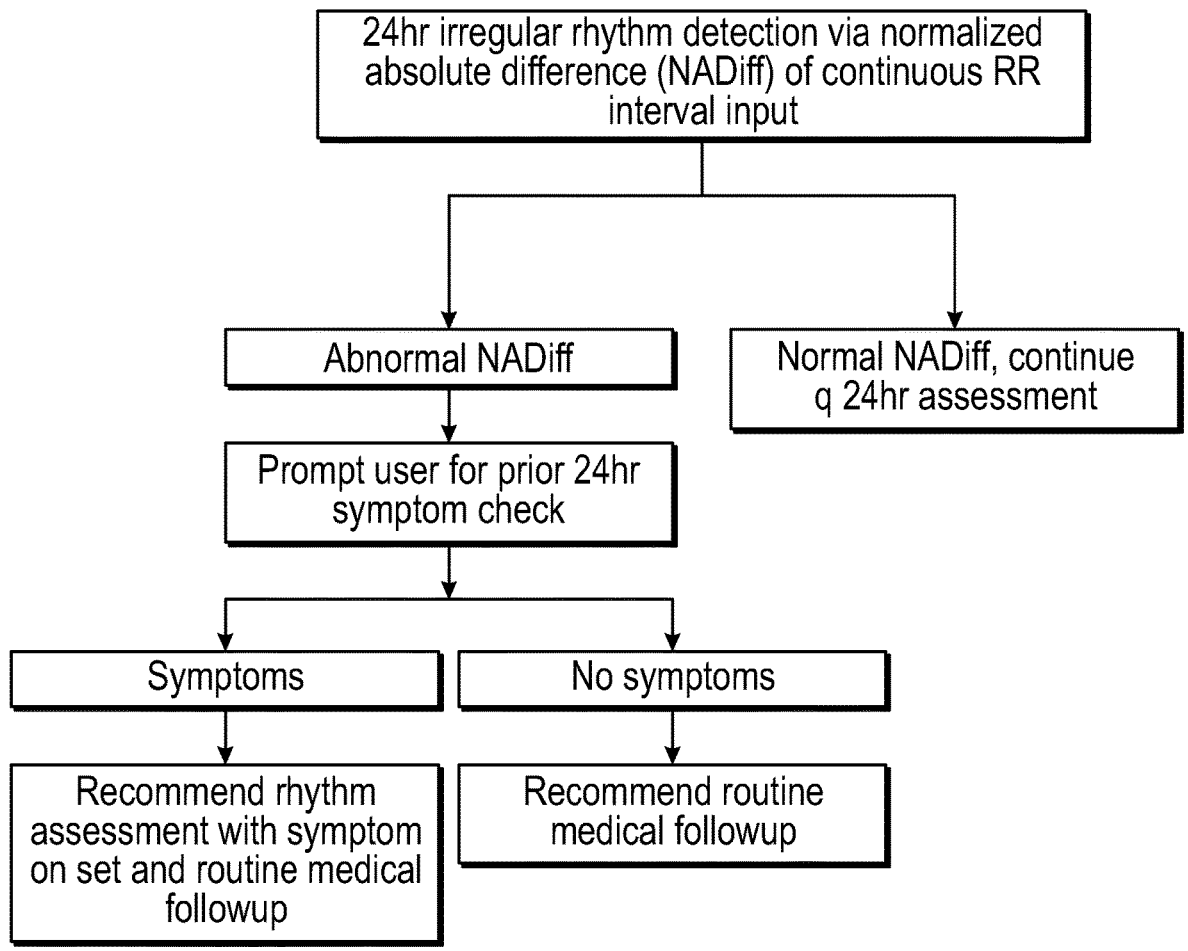
Figure 38:
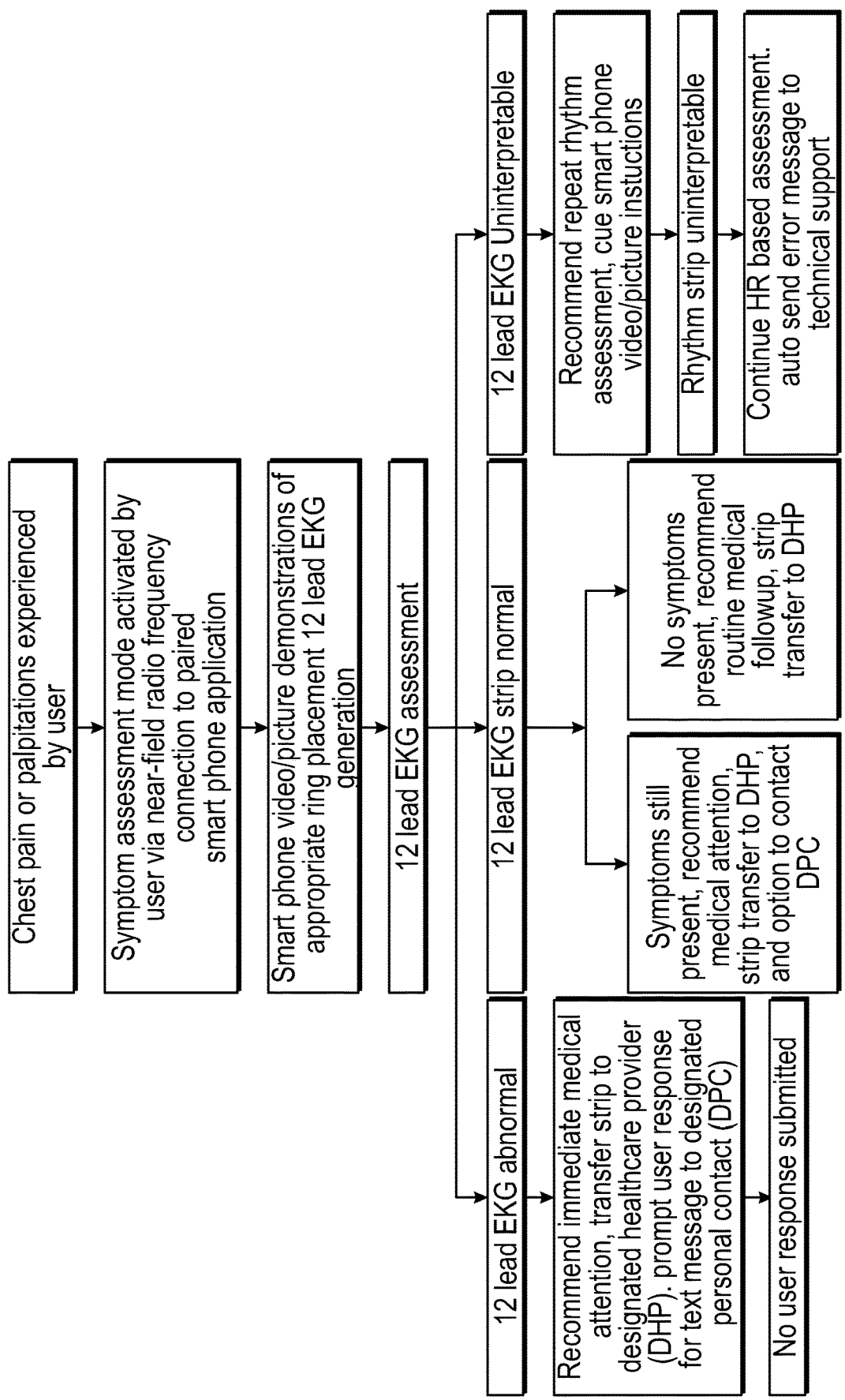

FIG. 37 illustrates a method of irregular rhythm detection over a prolonged period, such as 24 hours, using normalized absolute difference (NADiff) of continuous RR interval input (see WO 2009124187 A1, for example, for more information regarding the NADiff of continuous RR intervals, which is incorporated herein by reference). If a normal NADiff is detected, the method can continue periodic irregular rhythm assessment, such as every 24 hours. If an abnormal NADiff is detected, the method can prompt the wearer to check for any symptoms the wearer experienced during the prior time period, such as the last 24 hours. If not symptoms are reported, then the method can recommend routine medical follow-up evaluation, and if symptoms are detected, the method can recommend rhythm assessment with symptom onset and medical follow-up.

FIG. 39 illustrates a method following chest pain or palpitations experienced by the wearer, either following a prompt for symptoms or otherwise. If the wearer experiences chest pains or palpitations, the wearer can input that information using a smartphone app, or other input means. The method can assess the symptoms of the wearer and initiate a symptom assessment mode. The method can then cause the smartphone, or other device, to display videos/pictures/text instructions demonstrating placement of the wearable device at a series of EKG lead points on the wearer's body to produce a 12 lead EKG report, or other EKG report. The instructions provided to the wearer can give step-by-step instructions of where to place the palmar/ventral electrode against the wearer's body, how long to hold it, etc. The method can also control which of the electrodes to turn on for each lead placement and what polarity each electrode has for each lead placement. Once the EKG data is received, the method can assess the EKG data to determine if the EKG data is normal, abnormal, or uninterpretable. If the EKG data is abnormal, the method can recommend immediate medical attention and optionally transmit the EKG data to a designated healthcare provider. The method can also prompt the wearer for a message to a designated personal contact. If no user response is received, the method can try again, or else send a message to a secondary designated personal contact. If the EKG data is normal, the method can check if symptoms are still present. If symptoms are still present, the method can recommend medical attention and optionally transfer EKG data to a designated healthcare provider and/or message a designated personal contact. If no symptoms are present, the method can recommend routine medical follow-up and optionally transmit the EKG data to a designated healthcare provider. If the EKG data is uninterpretable, the method can recommend repeating the EKG generation and assessment steps to get new EKG data. If the new EKG is uninterpretable, the method can continue heart rate based assessment and optionally automatically send an error message to technical support personnel.

Any of the disclosed methods can be implemented using computing hardware and/or as computer-executable instructions stored on one or more computer-readable storage devices (e.g., one or more optical media discs, volatile memory components (such as DRAM or SRAM), or non-volatile memory components (such as flash memory or hard drives)) and executed on a computer (e.g., any commercially available computer, including smart phones or other mobile devices that include computing hardware). The term computer-readable storage device does not include communication connections, such as signals and carrier waves. Any of the computer-executable instructions for implementing the disclosed techniques as well as any data created and used during implementation of the disclosed embodiments can be stored on one or more computer-readable storage device. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers.

For clarity, only certain selected aspects of software-based implementations of the disclosed methods are described. Other details that are well known in the art are omitted. For example, the disclosed technology is not limited to any specific computer language or program. For instance, the disclosed technology can be implemented by software written in C++, Java, Perl, JavaScript, Adobe Flash, or any other suitable programming language. Likewise, the disclosed technology is not limited to any particular computer or type of hardware.

Any methods or functionality described herein can be performed, at least in part, by one or more hardware logic components, instead of software. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

The innovations disclosed herein may be implemented in diverse general-purpose or special-purpose computing systems. Exemplary suitable computing environments in which the described innovations may be implemented can comprise any of a variety of computing devices (e.g., desktop computer, laptop computer, server computer, tablet computer, media player, gaming system, smartphone, mobile device, etc.). For example, the computing environment can include one or more processing units and memory. The processing units can execute computer-executable instructions. A processing unit can be a general-purpose central processing unit (CPU), processor in an application-specific integrated circuit (ASIC) or any other type of processor. The system can include tangible memory, such as volatile memory (e.g., registers, cache, RAM), non-volatile memory (e.g., ROM, EEPROM, flash memory, etc.), or some combination of the two, accessible by the processing unit(s). The memory can store software for implementing one or more methods described herein, in the form of computer-executable instructions suitable for execution by the processing unit(s).

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Characteristics and features described in conjunction with a particular aspect, embodiment, or example of the disclosed technology are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the terms "a", "an", and "at least one" encompass one or more of the specified element. That is, if two of a particular element are present, one of these elements is also present and thus "an" element is present. For example, reference to "a sensor" includes a plurality of such sensors and equivalents thereof known to those skilled in the art, and so forth, and reference to "the sensor" is a reference to one or more such sensors and equivalents thereof known to those skilled in the art, and so forth. Recitation of ranges of values herein are merely intended to serve as a shorthand method of referring individually to each separate value falling within the range. Unless otherwise indicated herein, each separate value as well as intermediate ranges are incorporated herein as if it were individually recited herein.

The terms "a plurality of" and "plural" mean two or more of the specified element. As used herein, the term "and/or" used between the last two of a list of elements means any one or more of the listed elements. For example, the phrase "A, B, and/or C" means "A", "B,", "C", "A and B", "A and C", "B and C", or "A, B, and C." As used herein, the term "coupled" generally means physically or electrically or wirelessly coupled or linked and does not exclude the presence of intermediate elements between the coupled items absent specific contrary language.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim all that comes within the scope of the following claims and their equivalents.

The invention claimed is:

1. A cardiac monitoring system comprising:
  a wrist band comprising:
    a frame configured to be worn around a wrist of a wearer, the frame having an inner surface that faces the wrist and an outer surface that faces away from the wrist;
    a first electrode on the inner surface of the frame, wherein the first electrode is configured to detect a cardiovascular signal from the wrist;
    a second electrode positioned on a first portion of the outer surface of the frame, wherein the second electrode is configured to detect a cardiovascular signal from a finger of the wearer when the finger is touched against the second electrode while the wrist band is worn on the wrist, the finger being part of an arm of the wearer that does not include the wrist; and
    a third electrode positioned on a second portion of the outer surface of the frame, the second portion being opposite from the first portion such that the wrist is between the second and third electrodes, wherein the third electrode is configured to detect a cardiovascular signal from an EKG lead location on the wearer's body, apart from the wrist and the finger, when the third electrode is touched against the EKG lead location while the wrist band is worn on the wrist; and
a mobile computing device wirelessly connected to the wrist band and comprising a user interface,
wherein the wrist band is operable to simulate a 12-lead EKG measurement by touching the third electrode to a plurality of EKG lead locations on the wearer's body in series while simultaneously wearing the wrist band on the wrist and touching the finger to the second electrode, wherein the system is configured to simulate the 12-lead EKG measurement using at most five precordial lead readings, and wherein the mobile computing device is configured to display instructions to the wearer, via the user interface, to place the third electrode in contact with the plurality of EKG lead locations on the wearer's body in series.

2. The cardiac monitoring system of claim 1, wherein the EKG lead location on the wearer's body comprises a location on the wearer's chest.

3. The cardiac monitoring system of claim 1, wherein the EKG lead location on the wearer's body comprises a location on the wearer's leg.

4. The cardiac monitoring system of claim 1, wherein the wrist band is operable to continuously monitor the wearer's cardiovascular status to detect or predict cardiac arrhythmia in the wearer.

5. The cardiac monitoring system of claim 1, wherein the wrist band further comprises an additional sensor on the inner surface of the frame that measures blood oxygen saturation of the wearer.

6. The cardiac monitoring system of claim 1, wherein the wrist band further comprises an additional sensor on the inner surface of the frame that measures bioimpedance of the skin of the wrist or dry skin potential between two separated points on the skin of the wrist.

7. The cardiac monitoring system of claim 1, wherein the wrist band further comprises a button or other input device that can be activated to synch the wrist band to the mobile computing device via wireless communication.

8. The cardiac monitoring system of claim 1, wherein the wrist band further comprises a button or other input device that can be activated to initiate a cardiovascular measurement of the wearer.

9. The cardiac monitoring system of claim 1, wherein the wrist band further comprises a processor, memory, wireless communication device, and a power source.

10. The cardiac monitoring system of claim 1, wherein the wrist band further comprises a motion sensor or accelerometer.

11. The cardiac monitoring system of claim 1, wherein the wrist band further comprises a position sensor or orientation sensor.

12. The cardiac monitoring system of claim 1, wherein the wrist band further comprises a body temperature sensor.

13. The cardiac monitoring system of claim 1, wherein the wrist band further comprises a visual display screen.

14. The cardiac monitoring system of claim 1, wherein the wrist band further comprises a speaker or audio signal generator.

15. The cardiac monitoring system of claim 1, wherein the wrist band further comprises a vibratory or haptic signal generator.

16. The cardiac monitoring system of claim 1, wherein each of the first electrode and one or both of the second and third electrodes comprises a plurality of small bumps or teeth.

17. The cardiac monitoring system of claim 1, wherein the wrist band further comprises a detachable battery portion that is detachable from the frame of the band and wirelessly rechargeable.

18. The cardiac monitoring system of claim 17, wherein the wrist band further comprises a second battery that remains coupled to the frame when the detachable battery portion is detached from the frame.

19. The cardiac monitoring system of claim 17, wherein the detachable battery portion is annular.

20. The cardiac monitoring system of claim 1, wherein the cardiac monitoring system is operable to:
(i) continuously monitor the wearer's cardiovascular status with the wrist band to detect a potential cardiac event; and
(ii) responsive to detecting the potential cardiac event, display instructions to the wearer, via the user interface, to initiate a cardiovascular measurement with the wrist band.

21. The cardiac monitoring system of claim 1, wherein the cardiac monitoring system is operable to adjust a polarity status of one or more of the first electrode, the second electrode, and the third electrode for each EKG lead location of the plurality of EKG lead locations on the wearer's body.

22. A cardiac monitoring system comprising:
a wrist band comprising:
a frame configured to be worn around a wrist of a wearer, the frame having an inner surface that faces the wrist and an outer surface that faces away from the wrist;
a first electrode on the inner surface of the frame, wherein the first electrode is configured to detect a cardiovascular signal from the wrist;
a second electrode positioned on a first portion of the outer surface of the frame, wherein the second electrode is configured to detect a cardiovascular signal from a finger of the wearer when the finger is touched against the second electrode while the wrist band is worn on the wrist, the finger being part of an arm of the wearer that does not include the wrist;
a third electrode positioned on a second portion of the outer surface of the frame, the second portion being opposite from the first portion such that the wrist is between the second and third electrodes, wherein the third electrode is configured to detect a cardiovascular signal from an EKG lead location on the wearer's body, apart from the wrist and the finger, when the third electrode is touched against the EKG lead location while the wrist band is worn on the wrist; and
a detachable battery portion that is detachable from the frame and rechargeable; and
a mobile computing device wirelessly connected to the wrist band and comprising a user interface,
wherein the wrist band is operable to simulate a 12-lead EKG measurement by touching the third electrode to a plurality of EKG lead locations on the wearer's body in series while simultaneously wearing the wrist band on the wrist and touching the finger to the second electrode, and wherein the mobile computing device is configured to display instructions to the wearer, via the user interface, to place the third electrode in contact with the plurality of EKG lead locations on the wearer's body in series.

23. The cardiac monitoring system of claim 22, wherein the wrist band further comprises a second battery that remains coupled to the frame when the detachable battery portion is detached from the frame.

24. The cardiac monitoring system of claim 22, wherein the system is configured to simulate the 12-lead EKG measurement using at most five precordial lead readings.

* * * * *